(12) United States Patent
Xu et al.

(10) Patent No.: US 10,144,919 B2
(45) Date of Patent: Dec. 4, 2018

(54) PHOSPHOLIPASE C MUTANT AND USE THEREOF

(71) Applicant: Wilmar (Shanghai) Biotechnology Research & Development Center Co., LTD, Shanghai (CN)

(72) Inventors: Jun Xu, Shanghai (CN); Yaoji Xuan, Shanghai (CN); Jinmin Li, Shanghai (CN)

(73) Assignee: Wilmar (Shanghai) Biotechnology Research & Development Center Co., LTD (CN)

(*) Notice: Subject to any disclaimer, the term of this patent is extended or adjusted under 35 U.S.C. 154(b) by 67 days.

(21) Appl. No.: 15/035,105

(22) PCT Filed: Nov. 4, 2014

(86) PCT No.: PCT/CN2014/090213
§ 371 (c)(1),
(2) Date: May 6, 2016

(87) PCT Pub. No.: WO2015/067161
PCT Pub. Date: May 14, 2015

(65) Prior Publication Data
US 2016/0362665 A1    Dec. 15, 2016

(30) Foreign Application Priority Data

Nov. 7, 2013 (CN) .......................... 2013 1 0548632

(51) Int. Cl.
| | |
|---|---|
| *C12N 9/16* | (2006.01) |
| *C11B 3/00* | (2006.01) |
| *A23D 7/04* | (2006.01) |
| *A23D 9/04* | (2006.01) |
| *C12N 9/48* | (2006.01) |
| *C12N 9/20* | (2006.01) |

(52) U.S. Cl.
CPC ................ *C12N 9/16* (2013.01); *C11B 3/003* (2013.01); *C12N 9/20* (2013.01); *C12N 9/48* (2013.01); *C12Y 301/04003* (2013.01)

(58) Field of Classification Search
None
See application file for complete search history.

(56) References Cited

U.S. PATENT DOCUMENTS

| | | | |
|---|---|---|---|
| 7,977,080 B2 * | 7/2011 | Gramatikova | C12N 9/16 435/18 |
| 2002/0068325 A1 * | 6/2002 | Ng | C07K 14/395 435/69.1 |

FOREIGN PATENT DOCUMENTS

CN         102206616 A      10/2011

OTHER PUBLICATIONS

GenBank Database Accession No. WP_025279708, Jun. 2014, 1 page (Year: 2014).*
UniProt Accession No. P09598, Jun. 2012, 3 pages (Year: 2012).*
Daly et al., "Expression of heterologous proteins in Pichia pastoris: a useful experimental tool in protein engineering and production", J. Mol. Recognit. 18:119-138, 2005 (Year: 2005).*
Johansen, et al., "Cloning and sequencing of the gene encoding the phosphatidylcholine-preferring phospholipase C of Bacillus cereus", Gene. 65 (1988) pp. 293-304. © 1988 Elsevier Science Publishers B.V.
Rasko, D. A., et al., "GenBank Accession No: NP_977069.1", Hospholipase C [Bacillus cereus ATCC 10987] Jun. 10, 2013 (Jun. 10, 2013), see whole document.
Durban, et al., "High level expression of a recombinant phospholipase C from Bacillus cereus in Bacillus subtilis", Appl Microbiol Biotechnol (2007) 74: pp. 634-639.
Kook-Hwa Seo, et al., "High-level expression of recombinant phospholipase C from Bacillus cereus in Pichia pastoris and its characterization", Biotechnology Letters 26: pp. 1475-1479, 2004. © 2004 Kluwer Academic Publishers. Printed in the Netherlands.
Hough, et al., "High-resolution (1.5 A) crystal structure of phospholipase C from Bacillus cereus.", Nature. Mar. 23, 1989; 338(6213): pp. 357-360.

* cited by examiner

*Primary Examiner* — David Steadman
(74) *Attorney, Agent, or Firm* — St. Onge Steward Johnston & Reens, LLC

(57) ABSTRACT

The present application provides mutants of wild type phospholipase C (PLC) specific to phosphatidylcholine from *Bacillus cereus*. The related mutations include mutation of asparagine at position 63 to another amino acid, also including mutation of arginine at position 20 to histidine and of alanine at position 83 to aspartic acid. The present application also provides a nucleic acid molecule encoding the mutant, a vector containing the nucleic acid molecule, and a cell containing the nucleic acid molecule or vector. The present application also provides uses of the mutant, nucleic acid molecule vector, and cell.

5 Claims, 6 Drawing Sheets

Specification includes a Sequence Listing.

PHOSPHOLIPASE C MUTANT AND USE THEREOF

FIELD

The present application relates to mutants of phospholipase C that is specific to phosphatidylcholine, and use thereof.

REFERENCE TO SEQUENCE LISTING SUBMITTED ELECTRONICALLY

The official copy of the sequence listing was submitted electronically via EFS-Web as an ASCII formatted sequence listing with a file named 16U1949.TXT created on Aug. 19, 2016 and having a size of 91.7 kilobytes. This file replaces the one filed concurrently with the specification named 15R9767.TXT and having a file size of 83.6 kilobytes. The sequence listing contained in the ASCII formatted file is part of the specification and is herein incorporated by reference in its entirety.

BACKGROUND

Degumming is an important step in oil and fat refining. Traditional degumming by hydration is of high economic cost, high consumption of materials and energy and serious environmental pollution. As such, many works were devoted to apply a degumming by enzyme in the degumming step of oil and fat refining. As compared to the traditional method, the method of degumming by enzyme has great advantages in environmental protection, economic effect, and quality, etc., as it could improve economic benefits, reduce energy consumption and emission and reduce the ecological environment pollution. One kind of enzymes used in degumming of oil and fat is phospholipase. Phospholipase C (PLC) exhibits significant advantages in, such as increasing yield of diacylglycerols (DAG) and reducing loss of the produced oil, as compared to the other enzymes for degumming.

Phospholipase C specific to phosphatidylcholine from *Bacillus cereus* (BC-PC-PLC) is a phospholipase C that was studied early. BC-PC-PLC consists of 283 amino acids in its full length, with a signal peptide of 24 amino acids and a leader peptide of 14 amino acids. The mature peptide consists of 245 amino acids. See, such as, Johansen, T., Holm, T., Guddal, P. H., Sletten, K., Haugli, F. B., Little, C.(1988), "Cloning and sequencing of the gene encoding the phosphatidylcholine-preferring phospholipase C of *Bacillus cereus* " Gene 65(2):293-304).

The crystal structure of BC-PC-PLC have been reported, which consists of many helix domains and at least three $Zn^{2+}$ binding sites, with the catalytic site at the aspartic acid at position 55. See, such as, Hough., E., Hansen, L. K., Birknes, B., Jynge, K., Hansen, S., Hordvik, A., Little, C., Dodson, E., Derewenda, Z. (1989) "High-resolution (1.5 A) crystal structure of phospholipase C from *Bacillus cereus*." Nature. 338:357-60. Heterogenous expression of BC-PC-PLC was less studied. It has been reported that BC-PC-PLC was expressed in *Bacillus subtilis* and *pichia pastoris*. See, for example, Durban, M. A., Silbersack, J., Schweder, T., Schauer, F., Bornscheuer, U. T. (2007) High level expression of a recombinant phospholipase C from *Bacillus cereus* in *Bacillus subtilis*. Appl Microbiol Biotechnol 74(3):634-639; and Seo, K. H, Rhee J. I. (2004) High-level expression of recombinant phospholipase C from *Bacillus cereus* in *Pichia pastoris* and its characterization. Biotechnol Lett 26(19): 1475-1479.

Modified phospholipase C having, such as, a higher enzymatic activity, is desired in the art.

SUMMARY

In the first aspect, the present disclosure provides a polypeptide having an activity of phospholipase C specific to phosphatidylcholine, comprising a mutated amino acid sequence of SEQ ID NO: 2 or an active fragment thereof, wherein the mutation comprises mutating the asparagine at position 63 of the amino acid sequence set forth in SEQ ID NO: 2.

In some embodiments, the asparagine at position 63 of the amino acid sequence set forth in SEQ ID NO: 2 is mutated to serine (S), alanine (A), phenylalanine (F), histidine (H), lysine (K), arginine (R), tryptophan (W), tyrosine (Y), cysteine (C), aspartic acid (D), glutamic acid (E), glycine (G), isoleucine (I), leucine (L), methionine (M), glutamine (Q), threonine (T) or valine (V). In some embodiments, the asparagine at position 63 of the amino acid sequence set forth in SEQ ID NO: 2 is mutated to serine (S).

In some embodiments, the mutation further comprises mutating the arginine at position 20 of the amino acid sequence of SEQ ID NO: 2 to histidine and the alanine at position 83 of the amino acid sequence of SEQ ID NO: 2 to aspartic acid.

In some embodiments, the amino acid sequence of the polypeptide comprises an amino acid sequence selected from the group consisting of the amino acid sequence of SEQ ID NO: 8, 14, 16, 18, 20, 22, 24, 26, 28, 30, 32, 34, 38, 40, 42, 44, 46 and 48, or consists of an amino acid sequence selected from the group consisting of the amino acid sequence of SEQ ID NO: 8, 14, 16, 18, 20, 22, 24, 26, 28, 30, 32, 34, 38, 40, 42, 44, 46 and 48.

In some embodiments, the amino acid sequence of the polypeptide comprises the amino acid sequence set forth in SEQ ID NO: 12 or consists of the amino acid sequence set forth in SEQ ID NO: 12.

In the second aspect, the present disclosure provides a nucleic acid molecule encoding the polypeptide described in the first aspect.

The present disclosure also provides a nucleic acid molecule comprising a nucleic acid sequence selected from the group consisting of the nucleic acid sequences of SEQ ID NO: 7, 13, 15, 17, 19, 21, 23, 25, 27, 29, 31, 33, 37, 39, 41, 43, 45 and 47.

The present disclosure also provides a nucleic acid molecule comprising the nucleic acid sequence set forth in SEQ ID NO: 11.

In the third aspect, the present disclosure provides a vector containing the nucleic acid molecule described in the second aspect.

In some embodiments, the vector is an expression vector. In some embodiments, the vector is designed to be expressed in eukaryotic cells or prokaryotic cells. In some embodiments, the vector is designed to be expressed in bacterial cells, fungal cells, yeast cells, mammal cells, insect cells or plant cells.

In the fourth aspect, the present disclosure provides a cell containing the nucleic acid molecule described in the second aspect or the vector described in the third aspect. In some embodiments, the cell is a eukaryotic cell or a prokaryotic cell. In some embodiments, the cell is a bacterial cell, a fungal cell, a yeast cell, a mammal cell, an insect cell or a plant cell.

In the fifth aspect, the present disclosure provides a phospholipase C produced by the cell described in the fourth aspect.

In the sixth aspect, the present disclosure provides use of the polypeptide described in the first aspect, or the polypeptide encoded by the nucleic acid molecule described in the second aspect, or the polypeptide encoded by the vector described in the third aspect, or the polypeptide expressed by the cell described in the fourth aspect, or the phospholipase C described in the fifth aspect as a phosphatidylcholine-specific phospholipase C.

In some embodiments, the use is a use in the degumming of oil and fat.

In the seventh aspect, the present disclosure provides use of the polypeptide described in the first aspect, or the nucleic acid molecule described in the second aspect, or the vector described in the third aspect, or the cell described in the fourth aspect in the preparation of an enzyme for degumming.

DETAILED DESCRIPTION

Definition

Figure 1:
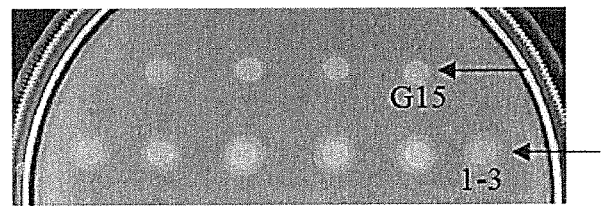
FIG. 1 shows the results obtained by culturing *Pichia pastoris* strains G15 and 1-3 expressing the wild-type BC-PC-PLC on the MM-yolk screening plate described in Example 1. The above four clones are strains G15 and the below six clones are strains 1-3. The strains were cultured at 30° C. for three days. The names of the strains are indicated just below the white sediment circles.

As used herein, phosphatidylcholine-specific phospholipase C and hosphatidylcholine-preferring phospholipase C have the same meaning and could readily be understood by the skilled artisan. As used herein, the abbreviation, PC-PLC, is meant to indicate phosphatidylcholine-specific phospholipase C and hosphatidylcholine-preferring phospholipase C. As used herein, one example of phosphatidylcholine-specific phospholipase C is the phosphatidylcholine-specific phospholipase C from *Bacillus cereus*, which is indicated by the abbreviation BC-PC-PLC in the context. It should be understood that, as used herein, the BC-PC-PLC is meant to indicate the wild type phosphatidylcholine-specific phospholipase C from *Bacillus cereus* and the mutants obtained in the present disclosure from the wild type phosphatidylcholine-specific phospholipase C.

The position of amino acid, indicated by number, corresponds to the position of amino acid in SEQ ID NO: 2. SEQ ID NO:2 indicates the amino acid sequence of the mature peptide of the wild type phosphatidylcholine-specific phospholipase C from *Bacillus cereus*.

Single letter or three letters for amino acid used herein are the internationally used abbreviations for amino acid.

As used herein, the terms "polypeptide", "peptide" and "protein" can be used interchangeable, indicating a polymer formed by many amino acids through peptide bond. Amino acid could be a naturally-occurring amino acid or an artificially synthesized analog.

Cell as used herein may be a eukaryotic cell or a Prokaryotic cell, including but is not limited to, for example bacterial cell, fungal cell, yeast cell, mammal cell, insect cell or plant cell.

Detailed Description of the Technical Solutions

The present disclosure provides mutants of phospholipase C obtained via a mutant screening method used in molecular biology, and used thereof. Specifically, the phospholipase C may be a phosphatidylcholine-specific phospholipase C (PC-PLC). More specifically, the phosphatidylcholine-specific phospholipase C may be a phosphatidylcholine-specific phospholipase C from *Bacillus cereus* (BC-PC-PLC).

In the first aspect, the present disclosure provides a polypeptide having an activity of phospholipase C specific to phosphatidylcholine, comprising a mutated amino acid sequence of SEQ ID NO: 2 or an active fragment thereof, wherein the mutation comprises mutating the asparagine at position 63 of the amino acid sequence set forth in SEQ ID NO: 2.

In some embodiments, the asparagine at position 63 of the amino acid sequence set forth in SEQ ID NO: 2 is mutated to alanine (A), cysteine (C), aspartic acid (D), glutamic acid (E), phenylalanine (F), glycine (G), histidine (H), isoleucine (I), lysine (K), leucine (L), methionine (M), glutamine (Q), arginine (R), threonine (T), valine (V), tryptophan (W) or tyrosine (Y). In some embodiments, the asparagine at position 63 of the amino acid sequence set forth in SEQ ID NO: 2 is mutated to serine (S).

In some embodiments, the mutation further comprises mutating the arginine at position 20 of the amino acid sequence of SEQ ID NO: 2 to histidine and the alanine at position 83 of the amino acid sequence of SEQ ID NO: 2 to aspartic acid.

In some embodiments, the amino acid sequence of the polypeptide comprises an amino acid sequence selected from the group consisting of the amino acid sequence of SEQ ID NO: 8, 14, 16, 18, 20, 22, 24, 26, 28, 30, 32, 34, 38, 40, 42, 44, 46 and 48, or consists of an amino acid sequence selected from the group consisting of the amino acid sequence of SEQ ID NO: 8, 14, 16, 18, 20, 22, 24, 26, 28, 30, 32, 34, 38, 40, 42, 44, 46 and 48. In some embodiments, the amino acid sequence of the polypeptide consists of an amino acid sequence selected from the group consisting of the amino acid sequence of SEQ ID NO: 8, 14, 16, 18, 20, 22, 24, 26, 28, 30, 32, 34, 38, 40, 42, 44, 46 and 48; in other words, the amino acid sequence of the polypeptide is different from the amino acid sequence of SEQ ID NO: 2 merely in the amino acid mutation at position 63.

In some embodiments, the amino acid sequence of the polypeptide comprises the amino acid sequence set forth in SEQ ID NO: 12 or consists of the amino acid sequence set forth in SEQ ID NO: 12. In some embodiments, the amino acid sequence of the polypeptide consists of the amino acid sequence set forth in SEQ ID NO: 12; in other words, the amino acid sequence of the polypeptide is different from the amino acid sequence of SEQ ID NO: 2 merely in that the amino acid residue at position 20 is mutated to histidine (H), the amino acid residue at position 63 is mutated to serine (S), and the amino acid residue at position 83 is mutated to aspartic acid (D), as described above.

In some embodiments, the length of the amino acid sequence of the polypeptide is identical to the length of the amino acid sequence set forth in SEQ ID NO: 2.

In some embodiments, the amino acid sequence of the polypeptide is longer than that of SEQ ID NO: 2. In some embodiments, the polypeptide further comprises a signal peptide and/or a leader peptide. As described in the Background part, the wide type phosphatidylcholine-specific phospholipase C from Bacillus cereus comprises a signal peptide, which consists of 24 amino acids, and a leader peptide, which consists of 14 amino acids. Therefore, the polypeptide of the present disclosure may contain the same or other signal peptide and/or leader peptide. In some embodiments, the signal peptide is an a-factor signal peptide. It should be understood by the skilled in the art that the polypeptide of the present disclosure may comprise the other functional elements, such as, but is not limited to, tag element for isolation and purification, such as histidine tag; selection element, such as selection based on antibiotics or fluorescence, for example, green fluorescent protein (GFP); etc.

In some embodiments, the amino acid sequence of the polypeptide is shorter than the amino acid sequence set forth in SEQ ID NO: 2. In the related embodiments, the polypeptide may contain an active fragment of the mutated amino acid sequence of SEQ ID NO: 2, such as the active fragment of the amino acid sequence set forth in SEQ ID NO: 8, 14, 16, 18, 20, 22, 24, 26, 28, 30, 32, 34, 38, 40, 42, 44, 46 or 48. As used herein, the term "active fragment" is meant to indicate a portion of the wild type phosphatidylcholine-specific phospholipase C or the present phosphatidylcholine-specific phospholipase C, which still retains the activity of the phosphatidylcholine-specific phospholipase C. The structure and functional sites of the wild type phosphatidylcholine-specific phospholipase C from Bacillus cereus were known in the art. Thus, the skilled artisan can readily prepare an active fragment of a polypeptide that retains the above mutation, such as a fragment retaining the functional domain. It is reported that the active sites of the PLC are Glu4, Asp55, Tyr56, Glu146, Ser64, Thr65, Phe66, Phe70, Ile80, Thr133, Asn134, Leu135, Ser143 (See, for example Hough., E., Hansen, L. K., Birknes, B., Jynge, K., Hansen, S., Hordvik, A., Little, C., Dodson, E., Derewenda, Z. (1989) "High-resolution (1.5 A) crystal structure of phospholipase C from Bacillus cereus." Nature. 338:357-60). According to the crystal structure of the PLC, the eighth and the ninth α helixes are present at amino acids 140-153 and amino acids 154-157, respectively, and the tenth a helix is present at amino acids 171-186. As such, the predictive active fragment is amino acids 1-170.

The functional variants of the polypeptide described in the first aspect are also contemplated in the present disclosure. In some embodiments, the functional variants are mutants by conservative substitution. The "conservative substitution" indicates changes in amino acid composition of a protein, which do not significantly change the activity of the protein. Therefore, the mutant by conservative substitution of a specific amino acid sequence is meant to refer to the substitution of the amino acid that is not critical to the activity of the protein, or to the substitution of an amino acid with another amino acid having a similar property, such as acidic, alkaline, positive charge-carrying or negative charge-carrying, polar or non-polar, which allows for substitution of critical amino acid without significant change of activity. The conservative substitution table providing functionally similar amino acid is well known in the art. For example, each group in the 6 groups provided in the following list contains the amino acids that are conservative to each other:

1) Alanine (A), Serine (S), Threonine (T);
2) Aspartic acid (D), Glutamic acid (E);
3) Asparagine (N), glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Also see, Creighton, *Proteins : Structures and Molecular Properties*, W. H. Freeman and Company, New York (2nd Ed., 1992).

In some embodiments, the functional variants have a sequence identity or similarity of at least 70%, at least 75%, at least 80%, at least 85%, at least 90%, at least 95%, at least 96%, at least 97%, at least 98%, at least 99%, or more, to the parent sequence, such as the amino acid set forth in SEQ ID NO: 8, 12, 14, 16, 18, 20, 22, 24, 26, 28, 30, 32, 34, 38, 40, 42, 44, 46 or 48.

In the second aspect, the present disclosure provides a nucleic acid molecule encoding the polypeptide described in the first aspect. Different nucleic acid molecules obtained due to degeneracy of genetic codon or preference to codon by different species are also contemplated in the present disclosure.

Nucleic acid molecules are also provided in the present disclosure, which contain a nucleic acid sequence selected from the group consisting of the nucleic acid sequences of SEQ ID NO: 7, 13, 15, 17, 19, 21, 23, 25, 27, 29, 31, 33, 37, 39, 41, 43, 45 and 47.

Nucleic acid molecule is also provided in the present disclosure, which contains the nucleic acid sequence set forth in SEQ ID NO: 11.

It should be understood that the nucleic acid molecules of the present disclosure can contain not only the coding sequence of the mutant of the BC-PL-PLC mature polypeptide, but also other nucleic acid sequence(s). In some embodiments, said other nucleic acid sequence may be the sequence encoding a signal peptide and/or a leader peptide. In some embodiments, said other nucleic acid sequence is a nucleic acid sequence encoding a tag element for isolation and purification, such as a histidine tag, or a nucleic acid sequence encoding a selection element, such as selection based on antibiotic or fluorescence, for example, green fluorescent protein (GFP). The skilled artisan can understand that said other nucleic acid also can be a regulatory sequence necessary for transcription and/or translation, such as a promoter, an enhancer, etc.

In the third aspect, the present disclosure provides a vector containing the nucleic acid molecule described in the second aspect. In some embodiments, the vector is an expression vector. In some embodiments, the vector is designed to be expressed in eukaryotic cells or prokaryotic cells. In some embodiments, the vector is designed to be expressed in bacterial cells, fungal cells, yeast cells, mammal cells, insect cells or plant cells. In some embodiments, the vector is a plasmid. Suitable vectors for eukaryotic cell or prokaryotic cell are well known in the art and many parent vectors are commercially available. Examples of vector include, but are not limited to, the vectors used in the Examples of the present disclosure.

In the fourth aspect, the present disclosure provides a cell containing the nucleic acid molecule described in the second aspect or the vector described in the third aspect. In some embodiments, the cell is a eukaryotic cell or a prokaryotic cell. In some embodiments, the cell is a bacterial cell, a fungal cell, a yeast cell, a mammal cell, an insect cell or a plant cell. In some embodiments, the cell is a cell of *Pichia pastoris*. In some embodiments, the cell is a cell of *Bacillus subtilis*. For the cell containing the nucleic acid molecule of the present disclosure, the nucleic acid molecule may be located outside the chromosome, such as in the vector, or may be integrated into the chromosome of the host cell. Techniques for integrating a nucleic acid molecule into the chromosome of a host cell and for transforming or transfecting a vector into a host cell are well known by the skilled artisan.

In the fifth aspect, the present disclosure provides a phospholipase C produced by the cell described in the fourth aspect. Techniques for producing a target polypeptide or protein by a genetically engineering host cell are well known in the art.

In the sixth aspect, the present disclosure provides use of the polypeptide described in the first aspect, or the polypeptide encoded by the nucleic acid molecule described in the second aspect, or the polypeptide encoded by the vector described in the third aspect, or the polypeptide expressed by the cell described in the fourth aspect, or the phospholipase C described in the fifth aspect as a phosphatidylcholine-specific phospholipase C. In some embodiments, the use is a use in the degumming of oil and fat. Use of a phosphatidylcholine-specific phospholipase C in the degumming process of oil and fat is known in the art. Phospholipase C can hydrolyze the colloid component, phospholipid, in the oil, to produce hydrophilic phosphoric acid and oleophylic DAG. The hydrophilic substance is removed by water, thereby removing the colloid. The yield of oil could be increased by the DAG. For example, in the degumming by enzyme, a solution of phospholipase C is added after the starting oil is heated to 60° C. After mixing by high velocity shearing, the mixture is allowed to react in a reactor under stirring for 2 hours. Then the water phase is isolated from the oil phase by centrifugation.

In the seventh aspect, the present disclosure provides use of the polypeptide described in the first aspect, or the nucleic acid molecule described in the second aspect, or the vector described in the third aspect, or the cell described in the fourth aspect in the preparation of an enzyme for degumming. Methods for preparing an enzyme for degumming by utilizing polypeptide, nucleic acid molecule, vector or transformed cell are well known in the art. Exemplified by fermentation, the isolated DNA sequence of a phospholipase C sequence may be transformed into a host cell, such as *Pichia pastori*, via an expression vector. Then the host cell is subjected to a large-scale fermentation in a fermentor. Fermentation liquid is obtained by filtration and the salt ions of high concentration in the fermentation liquid are removed by ultrafiltration by using a corresponding buffer for replacement. General stabilizer, such as glycerin, and zinc ions in a form of zinc sulfate, are added to the ultrafiltrate.

It should be understood that the above detailed descriptions merely serve for the purpose of allowing the skilled artisan to understand the content of the present disclosure clearly. They are not intended to limit the invention from any aspects. Various modification and change could be made to be the embodiments by the skilled artisan.

EXAMPLES

The following Examples are provided for further illustrating the present disclosure, which are not intended to limit the application.

Experimental Materials

The major materials used in the Examples of the disclosure are listed below:

1. Strain and Plasmid

Strain: *Pichia pastori* GS115 (Invitrogen, Art. No. C181-00), *E. coli* DH5a (TAKARA, Art. No. D9057A).

Plasmid: pPIC-9k (Invitrogen, Art. No. V17520), pA0815 (Invitrogen, Art. No. V18020); pAO-PLC vector and pAOmu-PLC vector were constructed by the inventors of the present application as detailedly described below.

2. Culture Medium and Solution

LB liquid culture medium: 0.5% yeast extract, 1% Casein Tryptone, 1% NaCl, pH 7.0.

LB solid culture medium: agar was added to the LB liquid culture medium to a concentration of 1.5%.

YPD liquid culture medium: 1% yeast extract, 2% Tryptone, 2% glucose.

YPD solid culture medium: agar was added to the YPD liquid culture medium to a concentration of 2%.

MGYS solid culture medium: 1.34% yeast nitrogen base (YNB) (containing ammonia sulfate, with amino acid-free), 1% glycerin, 1M sorbitol, $4 \times 10^{-5}$% D-biotin, 2% agar.

MM-yolk screening culture medium: 1.34% yeast nitrogen base (YNB) (containing ammonia sulfate, with amino acid-free), $4 \times 10^{-5}$% D-biotin, 0.5% methanol (added after sterilization), 2% yolk solution, 2% agar.

Preparation of yolk solution: one fresh egg was cleaned with 75% alcohol for sterilization. Sterile nipper was used to knock out egg shell to allow egg white to flow out. Yolk was washed by sterile water and then added to a triangular flask containing 80 ml sterile water and mixed homogenously to obtain 20% yolk solution.

BMGY liquid culture medium: 1% yeast extract, 2% Tryptone, 1.34% yeast nitrogen base (YNB) (containing ammonia sulfate, with amino acid-free), 1% glycerin, $4 \times 10^{-5}$% D-biotin, 0.1M monopotassium phosphate-dipotassium phosphate buffer (pH 6.0).

BMMY liquid culture medium: 1% yeast extract, 2% Tryptone, 1.34% yeast nitrogen base (YNB) (containing ammonia sulfate, with amino acid-free), 0.5% methanol (added after sterilization), $4 \times 10^{-5}$% D-biotin (added after sterilization), 0.1M monopotassium phosphate-dipotassium phosphate buffer (pH 6.0).

3. Reagents Used for Detecting the Activity of PLC by Molybdenum Blue Method

PLC reaction solution: 0.5% soybean phospholipid, 25 mM Tris-HCl pH 7.5, 5 mM $CaCl_2$.

CIAP reaction solution: 50 mM Tris-HCl pH 9.0, 10 mM $MgCl_2$, 1 U CIAP (purchased from Bao Biological Engineering (Dalian) Ltd.).

Color reaction solution for developing molybdenum blue: 100 μl CIAP reactant, 0.2% ascorbic acid, 0.1% ammonium molybdate (formulated by 30% $H_2SO_4$).

4. Reagents Used for Detecting Protein Concentration

Kit for detecting protein concentration by modified Bradford method, purchased from Shanghai Sangon Biological Engineering Ltd.

5. Enzyme

Restriction endonucleases HindIII, EcoRI, and AatII, purchased from New England Biolabs (Beijing) LTD.

Enzymes for PCR: TaKaRa Taq, PrimeSTAR®HS DNA polymerase, purchased from Bao Biological Engineering (Dalian) Ltd.

T4 DNA ligase, purchased from Fermentas Ltd.

Example 1

Construction of *Pichia pastori* Strain for Expressing the Wild Type BC-PC-PLC

DNA sequence of BC-PC-PLC (SEQ ID NO: 1) was designed according to the mature peptide sequence of phosphatidylcholine-specific phospholipase C from *Bacillus cereus* (PDB ID: 1AH7) and codon preference of *Pichia pastori*. An α-factor signal peptide sequence, the DNA sequence of which (bases 8-274 in SEQ ID NO: 3) is derived from the commercial *Pichia pastori* expression vector pPIC-9k, and a Kozak sequence (bases 1-7 in SEQ ID NO:3) from *Pichia pastori*, are fused at its 5' end, thereby obtaining the α-BC-PC-PLC DNA sequence (SEQ ID NO:3).

The α-BC-PC-PLC DNA sequence was provided to Shanghai Sangon Biological Engineering Ltd. for total gene synthesis to obtain a cloning vector pGEM-T-PLC containing the α-BC-PC-PLC DNA sequence. By using this vector as template, the PLC fragment was obtained through PCR amplification by using PrimeSTAR®HS DNA polymerase and primers AmPLC-3/AmPLC-4.

By using the expression vector pPIC-9k as template, an AOX1 prompter fragment (PAOX1) was obtained through PCR amplification by using PrimeSTAR®HS DNA polymerase and primers AmPLC-1/AmPLC-2.

PAOX1+PLC fused fragment was obtained through overlap PCR by using primers AmPLC-1/AmPLC-4 and PrimeSTAR®HS DNA polymerase.

The PAOX1+PLC fused fragment was cloned into pAO815 vector by utilizing the AatII and EcoRI restriction sites to obtain expression vector pAO-PLC. The pAO-PLC was linearized by SalI and recovered by gel electrophoresis, which was a fragment of about 8.5 kb. Competent cells of *Pichia pastori* GS115 strains were prepared by a LiAC method. The linearized pAO-PLC fragment was transformed into the GS115 competent cells by electroporation. The transformants were inoculated on MGYS plate for culture at 30° C. for 3 days. Monoclone on the plate was picked up and suspended in 5 μl sterile water. 0.5 μl of the suspension was inoculated on a MM-yolk screening plate. After culturing at 30° C. for 3 days, positive clones were observed with white sediment circles around the thallus. The expressed phospholipase C could degrade lecithin into phosphatidylcholine and water-insoluble diglyceride. The white sediment circle around colony on the MM-yolk screening plate was produced from the above reaction. The colony having more phospholipase C secreted or having higher specific activity of secreted phospholipase C had a relatively large white sediment circle.

Two positive strains were obtained, which were designated as G15 and 1-3, as shown in FIG. 1. The white sediment circle of G15 is relatively small while the white sediment circle of 1-3 was relatively large.

Example 2

Construction of BC-PC-PLC Mutant Library and Screening

A fragment of about 900 bp was obtained through PCR amplification by using the pAO-PLC vector as template, and PrimeSTAR®HS DNA polymerase and primers AmPLC-1/AOXH-2. A fragment of about 1.1 kb was obtained through PCR amplification by using the pAO-PLC vector as template, and PrimeSTAR®HS DNA polymerase and primers AOXH-3/AmPLC-4. The fragments of about 900 bp and about 1.1 kb obtained previously were used as template for the third PCR to amply and obtain a fragment of about 1.9 kb by using primers AmPLC-1/AmPLC-4 and PrimeSTAR®HS DNA polymerase.

The fragment of about 1.9 kb was cloned to pAO-PLC through the AatII and EcoRI restriction sites to obtain expression vector pmAO-PLC. In pmAO-PLC, one HindIII restriction site of pAO-PLC was mutated. Thus, merely the HindIII restriction site at the 5' end of the BC-PC-PLC sequence was retained, which allowed to use HindIII and EcoRI to clone the mutated fragment of BC-PC-PLC into pmAO-PLC.

An error-prone PCR was performed by using the pAO-PLC vector as template, TaKaRa Taq enzyme and primers EPPLC-1/EPPLC-2 to obtain a pool of mutated amplicons of about 755 bp. When performing the PCR, 0.3 mM $MnCl_2$ was additionally added. The resultant fragments were cloned into pmAO-PLC through the HindIII and EcoRI restriction sites and the resultant vectors were transformed into *E. coli* DH5α strain. As a result, totally 1×10⁴ BC-PC-PLC mutants were obtained.

Figure 2:
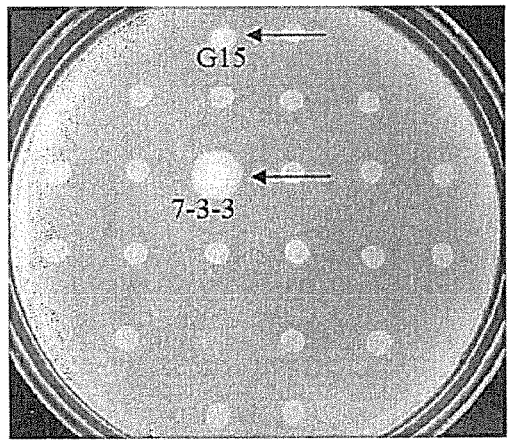
FIG. 2 shows the results obtained by culturing mutant strain 7-3-3 on the MM-yolk screening plate described in Example 2. The strains were cultured at 30° C. for two days. The names of the strains are indicated just below the white sediment circles.

Every 1×10³ BC-PC-PLC mutants were washed with 2 ml sterile water to 8 ml LB liquid culture medium supplemented with 100 pg/ml ampicillin and cultured at 37° C. for 4 hours. The plasmids were extracted and linearized by SalI. Fragments of about 8.5 kb were recovered. 500 ng vectors (the DNA was used as less as possible to ensure that most of the positive transformants contain one copy of the PLC gene) were transformed into the competent cells of *Pichia pastori* GS 115 strains by electroporation. The transformants were inoculated on MGYS plate for culture at 30° C. for 3 days to obtain a *Pichia pastori* mutant library of BC-PC-PLC. The monoclone on the plate was picked up and suspended in 5 μl sterile water. 0.5 μl of the suspension was inoculated on a MM-yolk screening plate. Using G15 as a control, the white sediment circle produced by the mutant was compared to that of G15. A mutant strain, designated as 7-3-3, which had a white sediment circle larger than that of G15 as shown in FIG. 2, was obtained.

Example 3

Analysis on the Sequence of the BC-PC-PLC Mutant

The 7-3-3 strain was inoculated on 3 ml YPD liquid culture medium and cultured at 30° C. overnight. The genomic DNA was extracted. The DNA sequence of BC-PC-PLC of the 7-3-3 strain was obtained by PCR amplification by using its genomic DNA as template, and PrimeSTAR®HS DNA polymerase and primers AOX1-5/AOX1-3. The resultant sequence was sent to Shanghai Sangon Biological Engineering Ltd. for sequencing by using primers AOX1-5/AOX1-3. The DNA sequencing result of the BC-PC-PLC from strain 7-3-3 was shown in SEQ ID NO: 4. As compared with SEQ ID NO: 3, SEQ ID NO: 4 contained 7 base mutations, 3 of which were sense mutations, including G to A at position 59, which resulted in mutation of arginine at position 20 to histidine (CGT→CAT); A to G at position 188, which resulted in mutation of asparagine at position 63 to serine (AAC→AGC); and C to A at position 248, which resulted in mutation of alanine at position 83 to aspartic acid (GCC→GAC).

Example 4

Construction of *Pichia pastori* Strain Expressing Mutant of BC-PC-PLC with One Mutation and Screening Example 4.1

Construction and Screening of PLC-R20H

A fragment of about 78 bp was obtained by PCR amplification by using pAO-PLC as template, PrimeSTAR®HS DNA polymerase and primers EPPLC-1/20RH-2. A fragment of about 707 bp was obtained by PCR amplification by using pAO-PLC as template, PrimeSTAR®HS DNA polymerase and primers 20RH-3/EPPLC-2. The fragments of about 78 bp and about 707 bp obtained previously were mixed to be used as template for the third PCR to amply and obtain a fragment of about 755 bp by using primers EPPLC-1/EPPLC-2 and PrimeSTAR®HS DNA polymerase.

Figure 3:
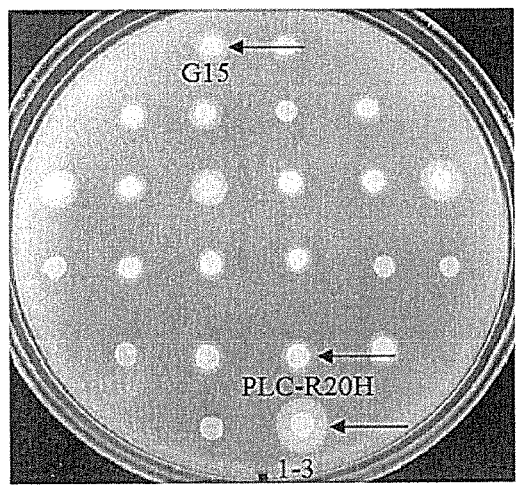
FIG. 3 shows the results obtained by culturing *Pichia pastoris* strain PLC-R20H expressing the BC-PC-PLC with point mutation on the MM-yolk screening plate described in Example 4. The strains were cultured at 30° C. for three days. The names of the strains are indicated just below the white sediment circles.

The fragment of about 755 bp was cloned into pmAO-PLC through the HindIII and EcoRI restriction sites to obtain a pmAO-PLC-R20H vector. The pmAO-PLC-R20H vector was linearized by SalI and a fragment of 8.5 kb was recovered by gel. Competent cells of *Pichia pastori* GS115 strains were prepared by a LiAC method. 500 ng of the linearized pmAO-PLC-R20H was transformed into the GS115 competent cells by electroporation. The transformants were inoculated on a MGYS plate for culture at 30° C. for 3 days. Monoclone was picked up from the plate and suspended in 5 μl sterile water. 0.5 μl of the suspension was inoculated on a MM-yolk screening plate. By using G15 and 1-3 as controls, the white sediment circle produced by the mutant was compared to those produced by G15 and 1-3, as shown in FIG. 3. The clone having no white sediment circle on the plate was a negative clone, i.e., the PLC gene fragment was not successfully transformed into the genome of that clone. When selecting the positive clone of the mutant for subsequent experiment, the clones which had a white sediment circle in the same or similar size and comprised a large proportion in all positive clones were firstly selected and then one of the clones was randomly picked up and designated as PLC-R20H for subsequent experiment. The mutant clone selected by such a way generally contained a single copy of the PLC gene. This was beneficial for reducing effect of difference in expression amount on the comparison of enzymatic activity.

Example 4.2

Construction and Screening of PLC-N63S

A fragment of about 207 bp was obtained by PCR amplification by using pAO-PLC as template, PrimeSTAR®HS DNA polymerase and primers EPPLC-1/63NS-2. A fragment of about 576 bp was obtained by PCR amplification by using pAO-PLC as template, PrimeSTAR®HS DNA polymerase and primers 63NS-3/EPPLC-2. The fragments of about 207 bp and about 576 bp obtained previously were mixed to be used as template for the third PCR to amply and obtain a fragment of about 755 bp by using primers EPPLC-1/EPPLC-2 and PrimeSTAR®HS DNA polymerase.

Figure 4:
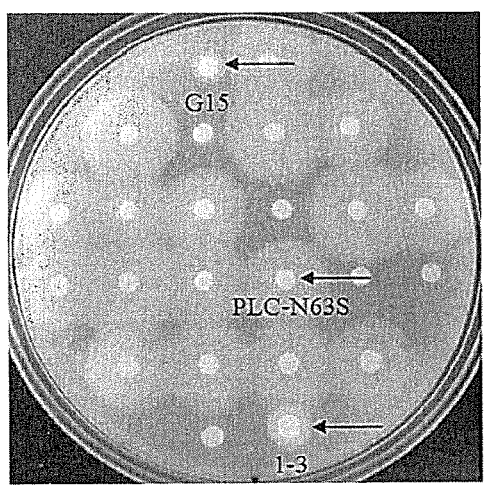
FIG. 4 shows the results obtained by culturing *Pichia pastoris* strain PLC-N63S expressing the BC-PC-PLC with point mutation on the MM-yolk screening plate described in Example 4. The strains were cultured at 30° C. for three days. The names of the strains are indicated just below the white sediment circles.

The fragment of about 755 bp was cloned into pmAO-PLC through the HindIII and EcoRI restriction sites to obtain a pmAO-PLC-N63S vector. The pmAO-PLC-N63S vector was linearized by SalI and a fragment of 8.5 kb was recovered. Competent cells of *Pichia pastori* GS115 strains were prepared by a LiAC method. 500 ng of the linearized pmAO-PLC-N63S was transformed into the GS115 competent cells by electroporation. The transformants were inoculated on a MGYS plate for culture at 30° C. for 3 days. Monoclone was picked up from the plate and suspended in 5 μl sterile water. 0.5 μl of the suspension was inoculated on a MM-yolk screening plate. By using G15 and 1-3 as controls, the white sediment circle produced by the mutant was compared to those produced by G15 and 1-3, as shown in FIG. 4. As described in Example 4.1, a positive clone for mutant PLC-N63S was picked up for subsequent experiment.

Example 4.3

Construction and Screening of PLC-A83D

A fragment of about 266 bp was obtained by PCR amplification by using pAO-PLC as template, and PrimeSTAR®HS DNA polymerase and primers EPPLC-1/83AD-2. A fragment of about 520 bp was obtained by PCR amplification by using pAO-PLC as template, PrimeSTAR®HS DNA polymerase and primers 83AD-3/EPPLC-2. The fragments of about 266 bp and about 520 bp obtained previously were mixed to be used as template for the third PCR to amply and obtain a fragment of about 755 bp by using primers EPPLC-1/EPPLC-2 and PrimeSTAR®HS DNA polymerase.

Figure 5:
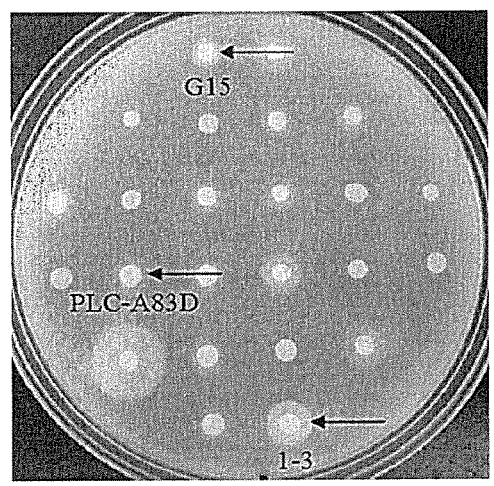
FIG. 5 shows the results obtained by culturing *Pichia pastoris* strain PLC-A83D expressing the BC-PC-PLC with point mutation on the MM-yolk screening plate described in Example 4. The strains were cultured at 30° C. for three days. The names of the strains are indicated just below the white sediment circles.

The fragment of about 755 bp was cloned into pmAO-PLC through the HindIII and EcoRI restriction sites to obtain a pmAO-PLC-A83S vector. The pmAO-PLC-A83S vector was linearized by SalI and a fragment of 8.5 kb was recovered. Competent cells of *Pichia pastori* GS115 strains were prepared by a LiAC method. 500 ng of the linearized pmAO-PLC-A83D was transformed into the GS115 competent cells by electroporation. The transformants were inoculated on a MGYS plate for culture at 30° C. for 3 days. Monoclone was picked up from the plate and suspended in 5 μl sterile water. 0.5 μl of the suspension was inoculated on a MM-yolk screening plate. By using G15 and 1-3 as controls, the white sediment circle produced by the mutant was compared to those produced by G15 and 1-3, as shown in FIG. 5. As described in Example 4.1, a positive clone for mutant PLC-A83D was picked up for subsequent experiment.

Example 4.4

Construction and Screening of PLC-R20HN63SA83D

A fragment of about 755 bp was obtained through PCR amplification by using the genomic DNA of the 7-3-3 strain as template, and PrimeSTAR®HS DNA polymerase and primers EPPLC-1/EPPLC-2.

Figure 6:
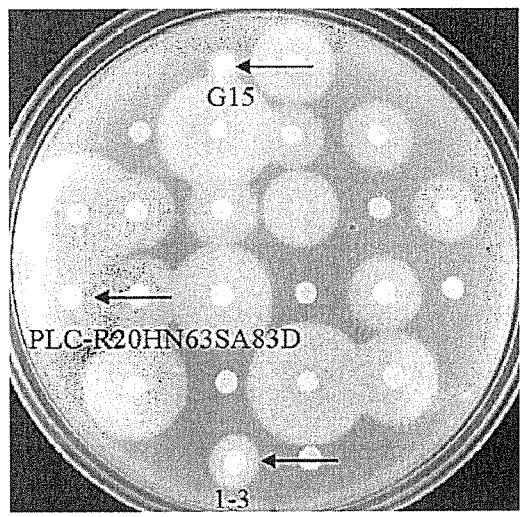
FIG. 6 shows the results obtained by culturing *Pichia pastoris* strain PLC-R20HN63SA83D expressing the BC-PC-PLC with point mutation on the MM-yolk screening plate described in Example 4. The strains were cultured at 30° C. for three days. The names of the strains are indicated just below the white sediment circles.

The fragment was cloned into pmAO-PLC through the HindIII and EcoRI restriction sites to obtain a pmAO-PLC-R20HN63SA83D vector. The pmAO-PLC-R20HN63SA83D vector was linearized by SalI and a fragment of 8.5 kb was recovered. Competent cells of *Pichia pastori* GS115 strains were prepared by a LiAC method. 500 ng of the linearized pmAO-PLC-R20HN63SA83D was transformed into the GS115 competent cells by electroporation. The transformants were inoculated on a MGYS plate for culture at 30° C. for 3 days. Monoclone on the plate was picked up and suspended in 5 μl sterile water. 0.5 μl of the suspension was inoculated on a MM-yolk screening plate. By using G15 and 1-3 as controls, the white sediment circle produced by the mutant was compared to those produced by G15 and 1-3, as shown in FIG. 6. As described in Example 4.1, a positive clone for mutant PLC-R20HN63SA83D was picked up for subsequent experiment.

The white sediment circle of the PLC-N63S mutant on the screening plate was comparable to that of the PLC-R20HN63SA83D clone and was obviously larger than the white sediment circles of G15 and 1-3. The white sediment circles of PLC-R20H and PLC-A83D are basically identical to the white sediment circles of G15 and 1-3. These results demonstrated that mutation of asparagine at position 63 to serine could improve the enzymatic activity of BC-PC-PLC.

Example 5

Fermentation of Strain Expressing the Mutant of BC-PC-PLC in Shake Flask

Strains G15, 1-3, PLC-R20H, PLC-N63S, PLC-A83D and PLC-R20HN63SA83D were respectively activated in liquid YPD, inoculated in a BMGY culture medium and cultured by oscillation at 30° C., 220rpm overnight. The culture was transferred to a BMMY culture with a initial $OD_{600}$ of 6.

Fermentation was initially induced by 2% methanol. 1% methanol was added respectively after 24 h and 32 h, and after 48 h and 56 h. Sampling was performed at 72 h. The obtained sample was subject to ultrafiltration for desalting by using an ultrafiltration tube having a molecular weight cutoff of 10 kDa. The treated sample was added into a buffer (20 mM citric acid-sodium citrate buffer (pH 6.6), 30% glycerin, 0.3% $ZnSO_4 \cdot 7H_2O$).

10 μl fermentation liquids were added to 190 μl PLC reaction solution containing 0.5% soybean phospholipid, 25 mM Tris-HCl pH 7.5 and 5 mM $CaCl_2$. The mixture was cultivated by oscillation at 37° C. for 30 min. After cultivation, 100 μl chloroform was added. The resultant mixture was mixed homogenously by oscillation and then centrifuged at 12000rpm for 2 min. 20 μl CIAP reaction solutions containing 50 mM Tris-HCl pH 9.0, 10 mM $MgCl_2$, and 1 U CIAP were added into 80 μl supernatants. The mixture was cultivated by oscillation at 37° C. for 1 h.

Figure 7:
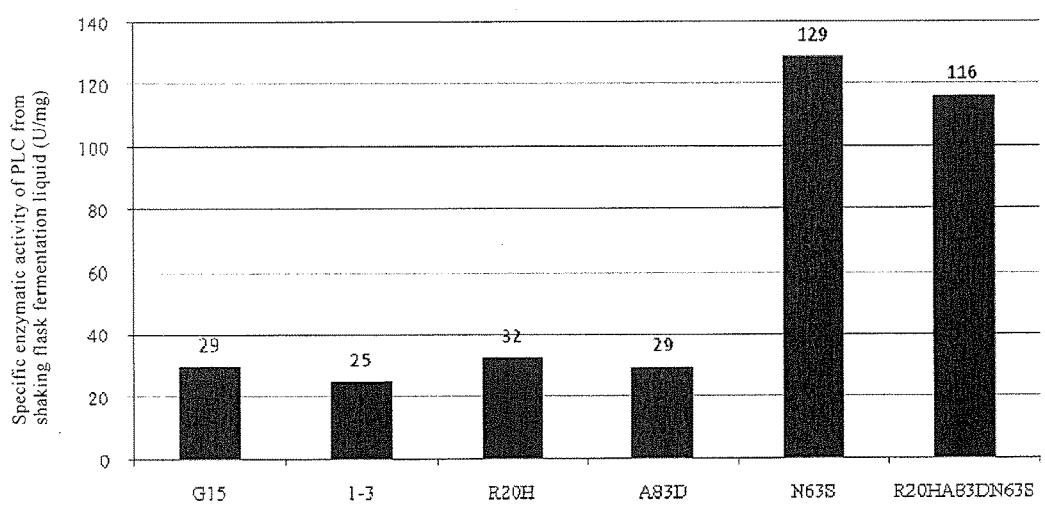
FIG. 7 shows the specific enzymatic activity of *Pichia pastoris* strains G15 and 1-3 expressing the wild-type BC-PC-PLC obtained in Example 1 and four *Pichia pastoris* strains expressing the BC-PC-PLC with point mutation obtained in Example 4.

After cultivation, 975 μl solutions for developing molybdenum blue containing 0.2% ascorbic acid and 0.1% ammonium molybdate were added into 25 μl reactants, and then the mixture was cultivated by oscillation at 37° C. for 10 min. Absorbance at 700 nm of the sample was detected and the activity of PLC in each fermentation liquid sample was calculated. The protein concentrations of the fermentation liquids from strains G15, 1-3, PLC-R20H, PLC-N63S, PLC-A83D and PLC-R20HN63SA83D fermented in shaking flask were detected by Bradford reagents, thereby obtaining the specific enzymatic activities of G15, 1-3, PLC-R20H, PLC-N63S, PLC-A83D and PLC-R20HN63SA83D. As shown in FIG. 7, the specific enzymatic activities of PLC-N63S and PLC-R20HN63SA83D were about four times of the wild type. The specific enzymatic activities of PLC-R20H and PLC-A83D were comparable to that of the wild type. These results demonstrated that mutation of asparagine at position 63 to serine was critical for improving the specific enzymatic activity.

Figure 8:
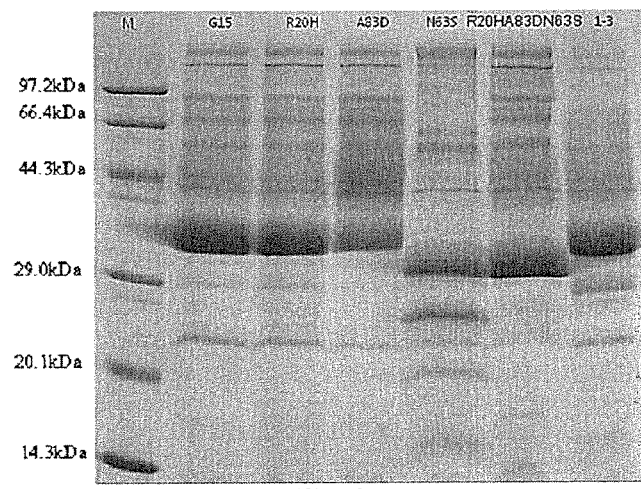
FIG. 8 shows the SDS-PAGE electrophoretogram of the fermentation liquids, in shake flask, of *Pichia pastoris* strains G15 and 1-3 expressing the wild-type BC-PC-PLC obtained in Example 1 and four *Pichia pastoris* strains expressing the BC-PC-PLC with point mutation obtained in Example 4.

The protein amounts in the fermentation liquids of G15, 1-3, PLC-R20H, PLC-N63S, PLC-A83D and PLC-R20HN63SA83D fermented in shaking flask were adjusted to the same level for SDS-PAGE electrophoresis. The results were shown in FIG. 8. The intensity of the PLC protein band for PLC-N63S is slightly lower than that of G15, indicating that the specific enzymatic activity of PLC-N63S was at least four times of that of G15.

Example 6

Construction and Shaking Flask Fermentation of PLC-N63S and PLC-R20HN63SA83D High-Producing Strains The pmAO-PLC-N63S and pmAO-PLC-R20HN63SA83D were linearized by SalI. A fragment of about 8.5 kb was recovered by gel electrophoresis. Competent cells of *Pichia pastori* GS115 strains were prepared by a LiAC method. 2 μg of the linearized pmAO-PLC-R20HN63SA83D was transformed into the GS115 competent cells by electroporation. The transformants were inoculated on a MGYS plate for culture at 30° C. for 3 days. Monoclone was picked up from the plate and suspended in 5 μl sterile water. 0.5 μl of the suspension was inoculated on a MM-yolk screening plate. 11 transformants, which had the largest white sediment circles, were picked up from 100 PLC-N63S transformants and named 6-1 to 6-11. Similarly, six transformants, which had the largest white sediment circles, were picked up from 100 PLC-R20HN63SA83D transformants and named 7-1 to 7-6.

Strains 6-1 to 6-11 and 7-1 to 7-6 were firstly activated in a liquid YPD, and then inoculated on a BMGY culture medium and cultivated by oscillation at 30° C., 220 rpm overnight. The culture was transferred to a BMMY culture medium with the initial $OD_{600}$ being 6.

Fermentation was initially induced by 2% methanol. 1% methanol was added respectively after 24 h and 32 h, and after 48 h and 56 h. Sampling was performed at 72 h. The obtained sample was subject to ultrafiltration for desalting by using an ultrafiltration tube having a molecular weight cutoff of 10 kDa. The treated sample was added into a buffer (20 mM citric acid-sodium citrate buffer (pH 6.6), 30% glycerin, 0.3% $ZnSO_4$. $7H_2O$).

Figure 9:
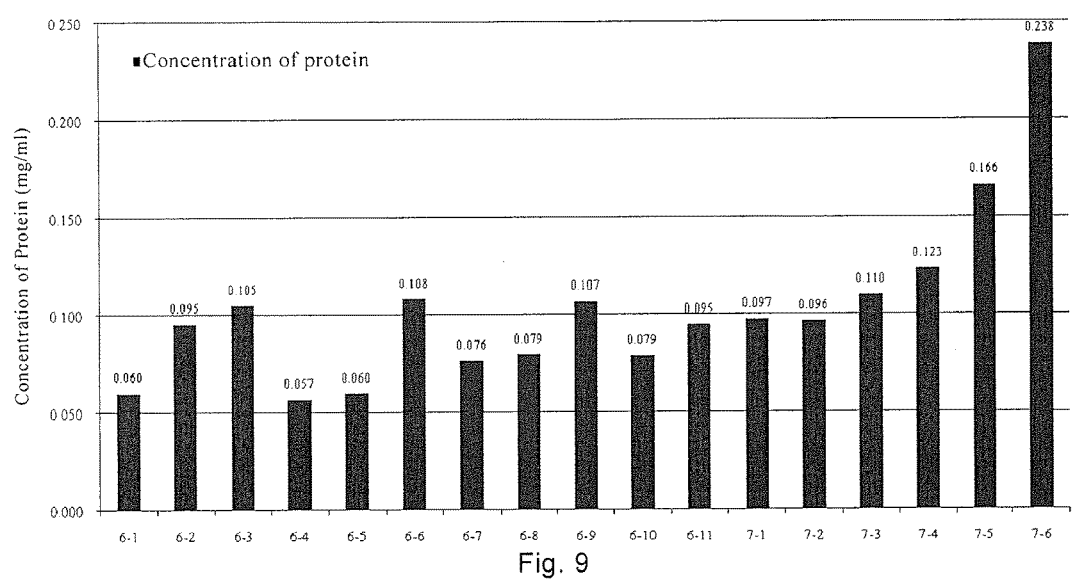
FIG. 9 shows the protein concentrations in the fermentation liquids, in shake flask, of the seventeen *Pichia pastoris* strains expressing the BC-PC-PLC with point mutation obtained in Example 6.

The protein concentrations of the fermentation liquids from strains 6-1 to 6-11 and 7-1 to 7-6 fermented in shaking flask were detected by Bradford reagents. The results were shown in FIG. 9.

Figure 10:
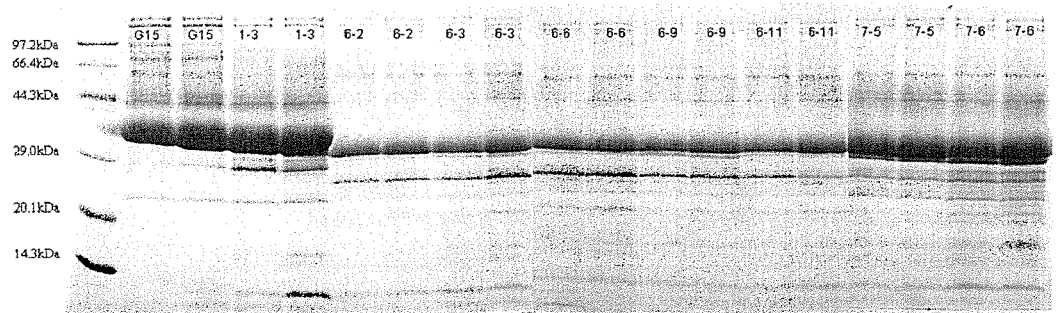
FIG. 10 shows the SDS-PAGE electrophoretogram of the fermentation liquids, in shake flask, of some *Pichia pastoris* strains expressing the BC-PC-PLC with point mutation obtained in Example 6.

Strain 6-6 had the highest protein concentration in the fermentation liquid among strains 6-1 to 6-11, which was 0.108mg/ml. Strain 7-6 had the highest protein concentration in the fermentation liquid among strains 7-1 to 7-6, which was 0.238 mg/ml. The strains having relatively high protein concentrations were picked up for SDS-PAGE electrophoresis, so as to compare the protein amount in their PLC target bands. The results were shown in FIG. 10. The intensity of PLC target bands for 7-5 and 7-6 was higher than those of 6-2, 6-3, 6-6, 6-9 and 6-11. These results demonstrated that R2OH and A83D within the PLC-R20HN63SA83D mutant were helpful in improving the expression amount of the mutant in *Pichia pastori*.

Example 7

Saturation Mutation at Position 63 of BC-PC-PLC

The asparagine at position 63 of BC-PC-PLC was respectively mutated to alanine (A), cysteine (C), aspartic acid (D), glutamic acid (E), phenylalanine (F), glycine (G), histidine (H), isoleucine (I), lysine (K), leucine (L), methionine (M), proline (P), glutamine (Q), arginine (R), threonine (T), valine (V), tryptophan (W) and tyrosine (Y).

In brief, a fragment of about 207 bp was obtained through PCR amplification by using the pAO-PLC vector as template, and PrimeSTAR®HS DNA polymerase and primers EPPLC-1/63X-2 (X indicates the single letter abbreviation of the above 18 amino acids). A fragment of about 576 bp was obtained through PCR amplification by using the pAO-PLC vector as template, and PrimeSTAR®HS DNA polymerase and primers 63X-3/EPPLC-2. The fragments of about 207 bp and about 576 bp obtained in the previous two PCR were mixed to be used as template for the third PCR to amply and obtain a fragment of about 755 bp by using primers EPPLC-1/EPPLC-2 and PrimeSTAR®HS DNA polymerase.

The resultant 18 fragments of about 755 bp were respectively cloned into pmAO-PLC through the HindIII and EcoRI restriction sites to obtain 18 pmAO-PLC-N63X vectors. The 18 pmAO-PLC-N63X vectors were linearized by SalI and fragments of 8.5 kb were recovered. Competent cells of *Pichia pastoris* GS115 strains were prepared by a LiAC method. 500 ng of the 18 linearized pmAO-PLC-N63X vectors were respectively transformed into the GS115 competent cells by electroporation. The transformants were inoculated on a MGYS plate for culture at 30° C. for 3 days. Monoclone on the plate was picked up and suspended in 5 μl sterile water. 0.5 μl of the suspension was inoculated on a MM-yolk screening plate. By using G15 and 1-3 as controls, the white sediment circle produced by the mutant was compared to those produced by G15 and 1-3. Positive clone for mutant PLC-N63X was picked up for subsequent experiment as described in Example 4.1. PLC-N63P, in which the amino acid at position 63 was mutated into proline, had no formation of white sediment circle, indicating that this mutation inactivated PLC.

Example 8

Enzymatic Activity and Heat Stability of the Strains Expressing the BC-PC-PLC Saturation Mutant in Shaking Flask Fermentation G15, 1-3, 6-6, 7-6, PLC-N63A, PLC-N63C, PLC-N63D, PLC-N63E, PLC-N63F, PLC-N63G, PLC-N63H, PLC-N63I, PLC-N63K, PLC-N63L, PLC-N63M, PLC-N63P, PLC-N63Q, PLC-N63R, PLC-N63T, PLC-N63V, PLC-N63W, and PLC-N63Y were firstly activated in a liquid YPD, and then inoculated in a BMGY culture medium and cultivated by oscillation at 30° C., 220 rpm overnight. The culture was transferred to a BMMY culture medium with the initial $OD_{600}$ being 6.

Fermentation was initially induced by 2% methanol. 1% methanol was added respectively after 24 h and 32 h, and after 48 h and 56 h. Sampling was performed at 72 h. The obtained sample was subject to ultrafiltration for desalting by using an ultrafiltration tube having a molecular weight cutoff of 10 kDa. The treated sample was added into a buffer (20 mM citric acid-sodium citrate buffer (pH 6.6), 30% glycerin, 0.3% $ZnSO_4$.$7H_2O$).

10 μl fermentation liquids were added to 190 μl PLC reaction solution containing 0.5% soybean phospholipid, 25 mM Tris-HCl pH 7.5 and 5 mM $CaCl_2$. The mixture was cultivated by oscillation at 37° C. or 60° C. for 30 min. After cultivation, 100 μl chloroform was added. The resultant mixture was mixed homogenously by oscillation and then centrifuged at 12000rpm for 2 min. 20 μl CIAP reaction solutions containing 50 mM Tris-HCl pH 9.0, 10 mM $MgCl_2$, and 1 U CIAP were added into 80 μl supernatants. The mixture was cultivated by oscillation at 37° C. for 1 h.

After cultivation, 975 μl solutions for developing molybdenum blue containing 0.2% ascorbic acid and 0.1% ammonium molybdate were added into 25 μl reactants, and then the mixture was cultivated by oscillation at 37° C. for 10 min. Absorbance at 700 nm of the sample was detected and the activity of PLC in each fermentation liquid sample was calculated.

The protein concentrations of the fermentation liquids from strains G15, 1-3, 6-6(PLC-N63S), 7-6, PLC-N63A, PLC-N63C, PLC-N63D, PLC-N63E, PLC-N63F, PLC-N63G, PLC-N63H, PLC-N63I, PLC-N63K, PLC-N63L, PLC-N63M, PLC-N63P, PLC-N63Q, PLC-N63R, PLC- N63T, PLC-N63V, PLC-N63W, and PLC-N63Y were detected by Bradford reagents.

Figure 11:
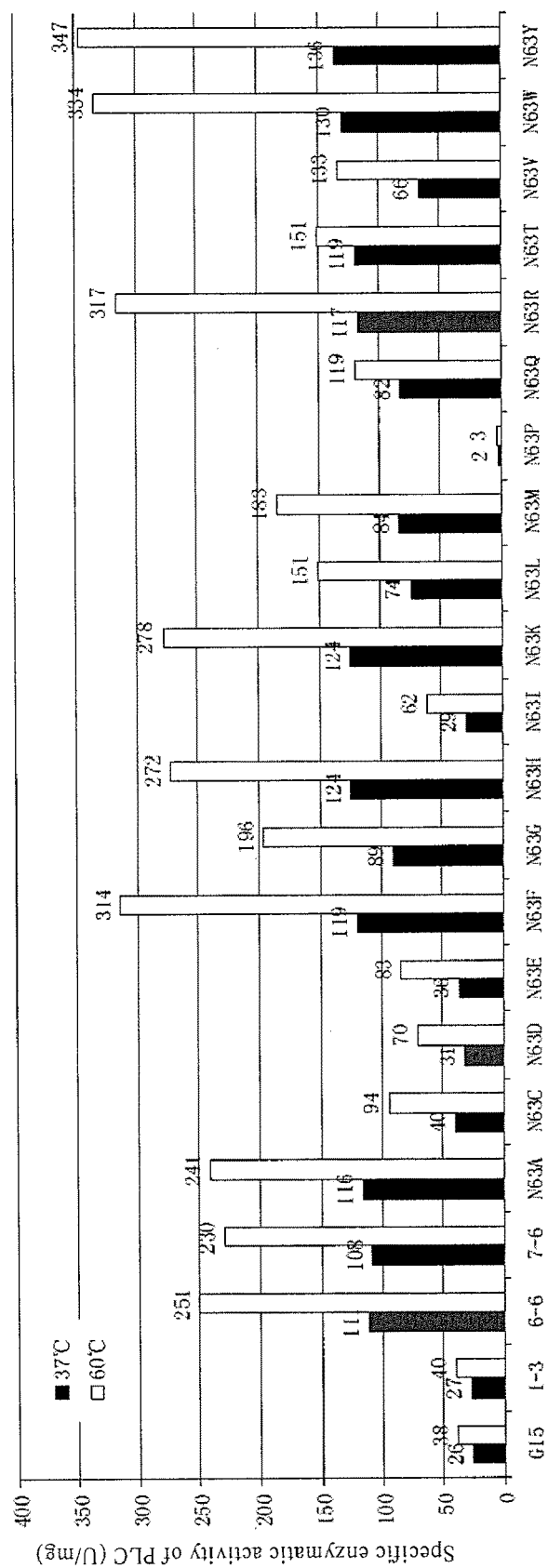
FIG. 11 shows the specific enzymatic activity of *Pichia pastoris* strains G15 and 1-3 expressing the wild-type BC-PC-PLC obtained in Example 1, *Pichia pastoris* strains 6-6 and 7-6 expressing the BC-PC-PLC with point mutation obtained in Example 6, and eighteen *Pichia pastoris* strains expressing the BC-PC-PLC with point mutation obtained in Example 8, reacted under 37° C. and 60° C.

The specific enzymatic activities of each mutant at 37° C. and 60° C. were thus obtained and shown in FIG. 11. From FIG. 11, it could be found that PLC-N63P had few activities at 37° C., and the specific enzymatic activities of PLC-N63C, PLC-N63D, PLC-N63E and PLC-N63I had no obvious enhancement. The specific enzymatic activities of other mutants had an improvement of more than 1 time as compared to the wild type. Especially, the specific enzymatic activities of PLC-N63S, PLC-N63A, PLC-N63F, PLC-N63H, PLC-N63K, PLC-N63R, PLC-N63T, PLC-N63W and PLC-N63Y were 4 times or more of that of the wild type.

When reacted at 60° C., PLC-N63P had few activities, and PLC-N63D and PLC-N63I had no obvious enhancement. The specific enzymatic activities of other mutants had an improvement of more than 1 time as compared to the wild type. Especially, the specific enzymatic activities of PLC-N63S, PLC-N63A, PLC-N63F, PLC-N63H, PLC-N63K, PLC-N63R, PLC-N63W and PLC-N63Y were 6 times or more of that of the wild type.

The specific enzymatic activity of the wild type at 60° C. was 1.5 times of the specific enzymatic activity at 37° C. However, the specific enzymatic activities of the mutants PLC-N63S, PLC-N63A, PLC-N63C, PLC-N63D, PLC-N63E, PLC-N63F, PLC-N63G, PLC-N63H, PLC-N63I, PLC-N63K, PLC-N63L, PLC-N63M, PLC-N63R, PLC-N63V, PLC-N63W and PLC-N63Y at 60° C. were 2 times or more of their specific enzymatic activities at 37° C., indicating that the mutants PLC-N63S, PLC-N63A, PLC-N63C, PLC-N63D, PLC-N63E, PLC-N63F, PLC-N63G, PLC-N63H, PLC-N63I, PLC-N63K, PLC-N63L, PLC-N63M, PLC-N63R, PLC-N63V, PLC-N63W and PLC-N63Y were more suitable for reaction at 60° C. than the wild type.

Figure 12:
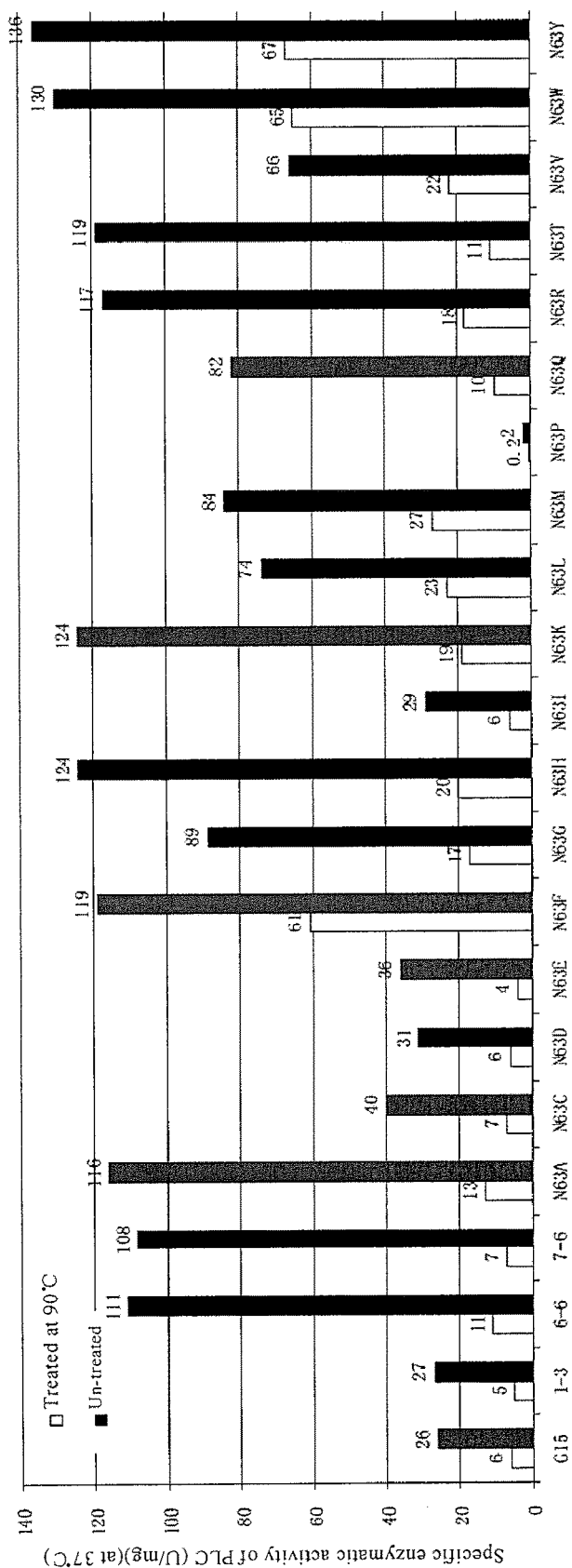
FIGS. 12 and 13 show the heat stability of *Pichia pastoris* strains G15 and 1-3 expressing the wild-type BC-PC-PLC obtained in Example 1, *Pichia pastoris* strains 6-6 and 7-6 expressing the BC-PC-PLC with point mutation obtained in Example 6, and eighteen *Pichia pastoris* strains expressing the BC-PC-PLC with point mutation obtained in Example 8.
Figure 13:
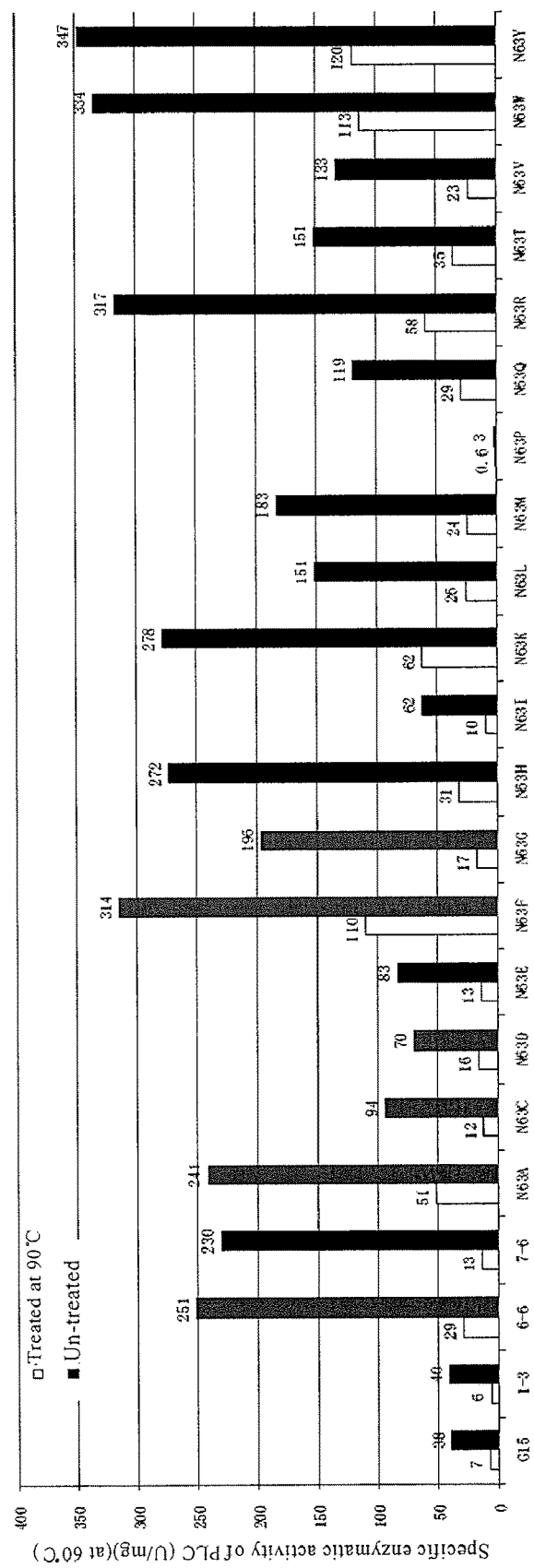

All fermentation liquids were cultivated at 90° C. for 1 h, and then reacted at 37° C. and 60° C. to detect the specific enzymatic activity after treated at 90° C. As shown in FIG. 12, after treated at 90° C. for 1 h, PLC-N63F, PLC-N63W and PLC-N63Y still retained 50% activity when reacted at 37° C., while the specific enzymatic activities of the wild type and other mutants were greatly reduced. As shown in FIG. 13, after treated at 90° C. for 1 h, PLC-N63F, PLC-N63W and PLC-N63Y still retained 30% activity when reacted at 60° C., while the specific enzymatic activities of the wild type and other mutants were greatly reduced. These results demonstrated that PLC-N63F, PLC-N63W and PLC-N63Y exhibited good heat stability.

From the above examples, it could be found that the specific enzymatic activities of the mutants of BC-PC-PLC at 37° C. and 60° C., in which the asparagine at position 63 was mutated to alanine (A), phenylalanine (F), glycine (G), histidine (H), isoleucine (I), lysine (K), leucine (L), methionine (M), glutamine (Q), arginine (R), threonine (T), serine (S), valine (V), tryptophan (W) or tyrosine (Y), had an improvement of more than 2 times than that of the wild type. After mutating to phenylalanine (F), tryptophan (W) and tyrosine (Y), the mutants exhibited good heat stability. Specifically, after treated at 90° C. for 1 h, these mutants retained about 50% specific enzymatic activities when reacted at 37° C. and about 30% specific enzymatic activities when reacted at 60° C., which were superior to the wild type and other mutants. Additionally, mutating arginine at position 20 of BC-PC-PLC to histidine and alanine at position 83 to aspartic acid could improve the expression amount of the mutant having the asparagine at position 63 mutated to serine in *Pichia pastori*.

DESCRIPTION OF SEQUENCE

SEQ ID NO:1: the DNA coding sequence of the wild type BC-PC-PLC;
SEQ ID NO:2: the amino acid sequence of the wild type BC-PC-PLC;
SEQ ID NO:3: the DNA sequence of the artificially synthesized α-BC-PC-PLC;
SEQ ID NO:4: the DNA coding sequence of the BC-PC-PLC mutant 7-3-3;
SEQ ID NO:5: the DNA coding sequence of the mutant PLC-R20H;
SEQ ID NO:6: the amino acid sequence of the mutant PLC-R20H;
SEQ ID NO:7: the DNA coding sequence of the mutant PLC-N63S;
SEQ ID NO:8: the amino acid sequence of the mutant PLC-N63S;
SEQ ID NO:9: the DNA coding sequence of the mutant PLC-A83D;
SEQ ID NO:10: the amino acid sequence mutant PLC-A83D;
SEQ ID NO:11: the DNA coding sequence of PLC-R20HN63SA83D;
SEQ ID NO:12: the amino acid sequence PLC-R20HN63SA83D;
SEQ ID NO:13: the DNA coding sequence of PLC-N63A;
SEQ ID NO:14: the amino acid sequence PLC-N63A;
SEQ ID NO:15: the DNA coding sequence of PLC-N63C;
SEQ ID NO:16: the amino acid sequence of PLC-N63C;
SEQ ID NO:17: the DNA coding sequence of PLC-N63D;
SEQ ID NO:18: the amino acid sequence of PLC-N63D;
SEQ ID NO:19: the DNA coding sequence of PLC-N63E;
SEQ ID NO:20: the amino acid sequence of PLC-N63E;
SEQ ID NO:21: the DNA coding sequence of PLC-N63F;
SEQ ID NO:22: the amino acid sequence of PLC-N63F;
SEQ ID NO:23: the DNA coding sequence of PLC-N63G;
SEQ ID NO:24: the amino acid sequence of PLC-N63G;
SEQ ID NO:25: the DNA coding sequence of PLC-N63H;
SEQ ID NO:26: the amino acid sequence of PLC-N63H;
SEQ ID NO:27: the DNA coding sequence of PLC-N63I;
SEQ ID NO:28: the amino acid sequence of PLC-N63I;
SEQ ID NO:29: the DNA coding sequence of PLC-N63K;
SEQ ID NO:30: the amino acid sequence of PLC-N63K;
SEQ ID NO:31: the DNA coding sequence of PLC-N63L;
SEQ ID NO:32: the amino acid sequence of PLC-N63L;
SEQ ID NO:33: the DNA coding sequence of PLC-N63M;
SEQ ID NO:34: the amino acid sequence of PLC-N63M;
SEQ ID NO:35: the DNA coding sequence of PLC-N63P;
SEQ ID NO:36: the amino acid sequence of PLC-N63P;
SEQ ID NO:37: the DNA coding sequence of PLC-N63Q;
SEQ ID NO:38: the amino acid sequence of PLC-N63Q;
SEQ ID NO:39: the DNA coding sequence of PLC-N63R;
SEQ ID NO:40: the amino acid sequence of PLC-N63R;
SEQ ID NO:41: the DNA coding sequence of PLC-N63T;
SEQ ID NO:42: the amino acid sequence of PLC-N63T;
SEQ ID NO:43: the DNA coding sequence of PLC-N63V;
SEQ ID NO:44: the amino acid sequence of PLC-N63V;
SEQ ID NO:45: the DNA coding sequence of PLC-N63W;
SEQ ID NO:46: the amino acid sequence of PLC-N63W;
SEQ ID NO:47: the DNA coding sequence of PLC-N63Y;
SEQ ID NO:48: the amino acid sequence of PLC-N63Y.

| List of the primer sequences | |
|---|---|
| Name of Primer (SEQ ID NO) | Primer Sequence (5'-3') |
| AmPLC-1 (SEQ ID NO: 49) | CCGGACGTCGCTAGCAGATCTAACATCCAAAGACG |
| AmPLC-2 (SEQ ID NO: 50) | TCATCGTTTCGCCTAGGATCCTTCGAATAATTAGTTG |
| AmPLC-3 (SEQ ID NO: 51) | GATCCTAGGCGAAACGATGAGATTTCCTTC |
| AmPLC-4 (SEQ ID NO: 52) | CCGGAATTCTTACCTGTCACCGTAAG |
| AOXH-2 (SEQ ID NO: 53) | GTTAAAATCAAAACGTTGTCAATTGGAACCAGTCG |
| AOXH-3 (SEQ ID NO: 54) | CCAATTGACAACGTTGATTTTAACGACTTTTAACGACAAC |
| AOX1-5 (SEQ ID NO: 55) | CGACTGGTTCCAATTGACAACG |
| AOX1-3 (SEQ ID NO: 56) | GGCAAATGGCATTCTGACATCCTC |
| EPPLC-1 (SEQ ID NO: 57) | CCCAAGCTTGGTCAGCTGAGGAC |
| EPPLC-2 (SEQ ID NO: 58) | CCGGAATTCTTACCTGTCACCGTA |
| 20RH-2 (SEQ ID NO: 59) | TATCAATGGCATGGTTCACGATCCATAAGTGAC |
| 20RH-3 (SEQ ID NO: 60) | GGATCGTGAACCATGCCATTGATATAATGTCTAGG |
| 63N5-2 (SEQ ID NO: 61) | CGAAGGTACTGCTATCGTAATAGGGGTTTTCATAATC |
| 63N5-3 (SEQ ID NO: 62) | CTATTACGATAGCAGTACCTTCGCTTCTCACTTTTAC |
| 83AD-2 (SEQ ID NO: 63) | CTTAGCTTGCTTGTCGAATGGGATATATGTCTTTCCG |
| 83AD-3 (SEQ ID NO: 64) | ATCCCATTCGACAAGCAAGCTAAGGAGACTG |
| 63A-2 (SEQ ID NO: 65) | CGAAGGTACTGGCATCGTAATAGGGGTTTTCATAATC |
| 63A-3 (SEQ ID NO: 66) | CTATTACGATGCCAGTACCTTCGCTTCTCAC |
| 63C-2 (SEQ ID NO: 67) | CGAAGGTACTGCAATCGTAATAGGGGTTTTCATAATC |
| 63C-3 (SEQ ID NO: 68) | CTATTACGATTGCAGTACCTTCGCTTCTCAC |
| 63D-2 (SEQ ID NO: 69) | CGAAGGTACTGTCATCGTAATAGGGGTTTTCATAATC |
| 63D-3 (SEQ ID NO: 70) | CTATTACGATGACAGTACCTTCGCTTCTCAC |
| 63E-2 (SEQ ID NO: 71) | CGAAGGTACTCTCATCGTAATAGGGGTTTTCATAATC |
| 63E-3 (SEQ ID NO: 72) | CTATTACGATGAGAGTACCTTCGCTTCTCACTTTTAC |
| 63F-2 (SEQ ID NO: 73) | CGAAGGTACTGAAATCGTAATAGGGGTTTTCATAATC |
| 63F-3 (SEQ ID NO: 74) | CTATTACGATTTCAGTACCTTCGCTTCTCAC |
| 63G-2 (SEQ ID NO: 75) | CGAAGGTACTACCATCGTAATAGGGGTTTTCATAATC |
| 63G-3 (SEQ ID NO: 76) | CTATTACGATGGTAGTACCTTCGCTTCTCACTTTTAC |
| 63H-2 (SEQ ID NO: 77) | CGAAGGTACTGTGATCGTAATAGGGGTTTTCATAATC |
| 63H-3 (SEQ ID NO: 78) | CTATTACGATCACAGTACCTTCGCTTCTCAC |
| 63I-2 (SEQ ID NO: 79) | CGAAGGTACTGATATCGTAATAGGGGTTTTCATAATC |
| 63I-3 (SEQ ID NO: 80) | CTATTACGATATCAGTACCTTCGCTTCTCAC |
| 63K-2 (SEQ ID NO: 81) | CGAAGGTACTCTTATCGTAATAGGGGTTTTCATAATC |
| 63K-3 (SEQ ID NO: 82) | CTATTACGATAAGAGTACCTTCGCTTCTCACTTTTAC |
| 63L-2 (SEQ ID NO: 83) | CGAAGGTACTCAAATCGTAATAGGGGTTTTCATAATC |
| 63L-3 (SEQ ID NO: 84) | CTATTACGATTTGAGTACCTTCGCTTCTCACTTTTAC |
| 63M-2 (SEQ ID NO: 85) | CGAAGGTACTCATATCGTAATAGGGGTTTTCATAATC |
| 63M-3 (SEQ ID NO: 86) | CTATTACGATATGAGTACCTTCGCTTCTCACTTTTAC |

List of the primer sequences

| Name of Primer (SEQ ID NO) | Primer Sequence (5'-3') |
|---|---|
| 63P-2 (SEQ ID NO: 87) | CGAAGGTACTTGGATCGTAATAGGGGTTTTCATAATC |
| 63P-3 (SEQ ID NO: 88) | CTATTACGATCCAAGTACCTTCGCTTCTCACTTTTAC |
| 63Q-2 (SEQ ID NO: 89) | CGAAGGTACTTTGATCGTAATAGGGGTTTTCATAATC |
| 63Q-3 (SEQ ID NO: 90) | CTATTACGATCAAAGTACCTTCGCTTCTCACTTTTAC |
| 63R-2 (SEQ ID NO: 91) | CGAAGGTACTTCTATCGTAATAGGGGTTTTCATAATC |
| 63R-3 (SEQ ID NO: 92) | CTATTACGATAGAAGTACCTTCGCTTCTCACTTTTAC |
| 63T-2 (SEQ ID NO: 93) | CGAAGGTACTGGTATCGTAATAGGGGTTTTCATAATC |
| 63T-3 (SEQ ID NO: 94) | CTATTACGATACCAGTACCTTCGCTTCTCAC |
| 63V-2 (SEQ ID NO: 95) | CGAAGGTACTGACATCGTAATAGGGGTTTTCATAATC |
| 63V-3 (SEQ ID NO: 96) | CTATTACGATGTCAGTACCTTCGCTTCTCAC |
| 63W-2 (SEQ ID NO: 97) | CGAAGGTACTCCAATCGTAATAGGGGTTTTCATAATC |
| 63W-3 (SEQ ID NO: 98) | CTATTACGATTGGAGTACCTTCGCTTCTCACTTTTAC |
| 63Y-2 (SEQ ID NO: 99) | CGAAGGTACTGTAATCGTAATAGGGGTTTTCATAATC |
| 63Y-3 (SEQ ID NO: 100) | CTATTACGATTACAGTACCTTCGCTTCTCAC |

The invention claimed is:

1. A mutant polypeptide having phosphatidylcholine-specific phospholipase C activity,
   wherein said mutant polypeptide comprises the amino acid sequence of SEQ ID NO: 2 or a fragment of the amino acid sequence of SEQ ID NO: 2 having phosphatidylcholine-specific phospholipase C activity,
   except the asparagine corresponding to position 63 of SEQ ID NO: 2 is mutated to serine (S), alanine (A), phenylalanine (F), histidine (H), lysine (K), arginine (R), tryptophan (W), tyrosine (Y), cysteine (C), aspartic acid (D), glutamic acid (E), glycine (G), isoleucine (I), leucine (L), methionine (M), glutamine (Q), threonine (T) or valine (V) in the amino acid sequence of the mutant polypeptide,
   the arginine corresponding to position 20 of SEQ ID NO: 2 is mutated to histidine in the amino acid sequence of the mutant polypeptide, and
   the alanine corresponding to position 83 of SEQ ID NO: 2 is mutated to aspartic acid in the amino acid sequence of the mutant polypeptide.

2. The mutant polypeptide of claim 1, wherein the asparagine corresponding to position 63 of SEQ ID NO: 2 is mutated to serine (S), alanine (A), phenylalanine (F), histidine (H), lysine (K), arginine (R), tryptophan (W), or tyrosine (Y) in the amino acid sequence of the mutant polypeptide.

3. The mutant polypeptide of claim 1, wherein the amino acid sequence of the polypeptide comprises the amino acid sequence of SEQ ID NO: 12 or consists of the amino acid sequence of SEQ ID NO: 12.

4. A method of degumming of oil and fat, the method comprising contacting the oil and fat with the mutant polypeptide of claim 1, thereby degumming the oil and fat.

5. The method of claim 4, wherein the amino acid sequence of the mutant polypeptide comprises the amino acid sequence of SEQ ID NO: 12 or consists of the amino acid sequence of SEQ ID NO: 12.

* * * * *

SEQUENCE LISTING

<160> NUMBER OF SEQ ID NOS: 100

<210> SEQ ID NO 1
<211> LENGTH: 738
<212> TYPE: DNA
<213> ORGANISM: Pichia pastoris

<400> SEQUENCE: 1

```
tggtcagctg aggacaagca taaggaaggt gtgaatagtc acttatggat cgtgaaccgt    60
gccattgata taatgtctag gaatacaact ctggttaagc aagatagagt tgctcaattg   120
aatgaatggc gtacagagct agagaatggc atctacgctg ctgattatga aaacccctat   180
tacgataaca gtaccttcgc ttctcacttt tacgatccag acaacggaaa gacatatatc   240
ccattcgcca agcaagctaa ggagactgga gctaagtact tcaagttggc tggagagtca   300
tacaagaata aagacatgaa gcaggccttc ttttatcttg ggttgtcatt gcattatttg   360
ggcgatgtca accaacctat gcatgccgca aactttacga acctgtccta tccacagggt   420
tttcactcca gtacgagaa ctttgtcgat actattaaag acaactacaa agttaccgat   480
gggaacggat attggaattg gaaaggcacc aaccctgaag aatggattca cggtgcagca   540
gtagttgcaa acaggacta ctctggaatt gtcaatgaca ataccaaaga ttggtttgtg   600
aaagccgcag tctcccagga atatgcagat aaatggagag ctgaagttac acctatgact   660
ggtaaacgac taatggatgc ccaaagagtt actgctggtt acattcaatt atggttcgac   720
acttacggtg acaggtaa                                                 738
```

<210> SEQ ID NO 2
<211> LENGTH: 245
<212> TYPE: PRT

<213> ORGANISM: Pichia pastoris

<400> SEQUENCE: 2

```
Trp Ser Ala Glu Asp Lys His Lys Glu Gly Val Asn Ser His Leu Trp
1               5                   10                  15
Ile Val Asn Arg Ala Ile Asp Ile Met Ser Arg Asn Thr Thr Leu Val
            20                  25                  30
Lys Gln Asp Arg Val Ala Gln Leu Asn Glu Trp Arg Thr Glu Leu Glu
        35                  40                  45
Asn Gly Ile Tyr Ala Ala Asp Tyr Glu Asn Pro Tyr Tyr Asp Asn Ser
    50                  55                  60
Thr Phe Ala Ser His Phe Tyr Asp Pro Asp Asn Gly Lys Thr Tyr Ile
65                  70                  75                  80
Pro Phe Ala Lys Gln Ala Lys Glu Thr Gly Ala Lys Tyr Phe Lys Leu
                85                  90                  95
Ala Gly Glu Ser Tyr Lys Asn Lys Asp Met Lys Gln Ala Phe Phe Tyr
            100                 105                 110
Leu Gly Leu Ser Leu His Tyr Leu Gly Asp Val Asn Gln Pro Met His
        115                 120                 125
Ala Ala Asn Phe Thr Asn Leu Ser Tyr Pro Gln Gly Phe His Ser Lys
    130                 135                 140
Tyr Glu Asn Phe Val Asp Thr Ile Lys Asp Asn Tyr Lys Val Thr Asp
145                 150                 155                 160
Gly Asn Gly Tyr Trp Asn Trp Lys Gly Thr Asn Pro Glu Glu Trp Ile
                165                 170                 175
His Gly Ala Ala Val Val Ala Lys Gln Asp Tyr Ser Gly Ile Val Asn
            180                 185                 190
Asp Asn Thr Lys Asp Trp Phe Val Lys Ala Ala Val Ser Gln Glu Tyr
        195                 200                 205
Ala Asp Lys Trp Arg Ala Glu Val Thr Pro Met Thr Gly Lys Arg Leu
    210                 215                 220
Met Asp Ala Gln Arg Val Thr Ala Gly Tyr Ile Gln Leu Trp Phe Asp
225                 230                 235                 240
Thr Tyr Gly Asp Arg
                245
```

<210> SEQ ID NO 3
<211> LENGTH: 1012
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: alpha-BC-PC-PLC DNA

<400> SEQUENCE: 3

```
cgaaacgatg agatttcctt caattttttac tgcagttttta ttcgcagcat cctccgcatt      60
agctgctcca gtcaacacta aacagaaga tgaaacggca caaattccgg ctgaagctgt       120
catcggttac tcagatttag aaggggattt cgatgttgct gttttgccat tttccaacag      180
cacaaataac gggttattgt ttataaatac tactattgcc agcattgctg ctaaagaaga      240
agggtatct cttgagaaaa gagaggctga agcttggtca gctgaggaca agcataagga       300
aggtgtgaat agtcacttat ggatcgtgaa ccgtgccatt gatataatgt ctaggaatac      360
aactctggtt aagcaagata gagttgctca attgaatgaa tggcgtacag agctagagaa      420
```

-continued

| | |
|---|---|
| tggcatctac gctgctgatt atgaaaaccc ctattacgat aacagtacct tcgcttctca | 480 |
| cttttacgat ccagacaacg gaaagacata tatcccattc gccaagcaag ctaaggagac | 540 |
| tggagctaag tacttcaagt tggctggaga gtcatacaag aataaagaca tgaagcaggc | 600 |
| cttctttat cttgggttgt cattgcatta tttgggcgat gtcaaccaac ctatgcatgc | 660 |
| cgcaaacttt acgaacctgt cctatccaca gggttttcac tccaagtacg agaactttgt | 720 |
| cgatactatt aaagacaact acaaagttac cgatgggaac ggatattgga attggaaagg | 780 |
| caccaacccct gaagaatgga ttcacggtgc agcagtagtt gcaaacagg actactctgg | 840 |
| aattgtcaat gacaatacca aagattggtt tgtgaaagcc gcagtctccc aggaatatgc | 900 |
| agataaatgg agagctgaag ttacacctat gactggtaaa cgactaatgg atgcccaaag | 960 |
| agttactgct ggttacattc aattatggtt cgacacttac ggtgacaggt aa | 1012 |

<210> SEQ ID NO 4
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: BC-PC-PLC from strain 7-3-3

<400> SEQUENCE: 4

| | |
|---|---|
| tggtcagctg aggacaagca taaggaaggt gtgaatagtc acttatggat cgtgaaccat | 60 |
| gccattgata taatgtctag gaatacaact ctggttaagc aagatagagt tgctcaattg | 120 |
| aatgaatggc gaacagagct agagaatggc atctacgctg ctgattatga aaacccctat | 180 |
| tacgatagca gtaccttcgc ttctcacttt tacgatccag acaacggaaa gacatatatc | 240 |
| ccattcgaca agcaagctaa ggagactgga gctaagtact tcaagttggc tggagagtca | 300 |
| tacaagaata agacatgaa gcaggccttc ttttatcttg gttgtcatt gcattatttg | 360 |
| ggcgatgtca accaacctat gcatgccgca aactttacga acctgtccta tccacagggt | 420 |
| tttcactcca gtacgagaa cttcgtcgat actattaaag acaactacaa agttaccgat | 480 |
| gggaacggat attggaattg gaaaggcacc aaccctgagg aatggattca cggtgcagca | 540 |
| gtagtcgcaa acaggacta ctctggaatt gtcaatgaca ataccaaaga ttggtttgtg | 600 |
| aaagccgcag tctcccagga atatgcagat aaatggagag ctgaagttac acctatgact | 660 |
| ggtaaacgac taatggatgc ccaaagagtt actgctggtt acattcaatt atggttcgac | 720 |
| acttacggtg acaggtaa | 738 |

<210> SEQ ID NO 5
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of the mutant PLC-R20H

<400> SEQUENCE: 5

| | |
|---|---|
| tggtcagctg aggacaagca taaggaaggt gtgaatagtc acttatggat cgtgaaccat | 60 |
| gccattgata taatgtctag gaatacaact ctggttaagc aagatagagt tgctcaattg | 120 |
| aatgaatggc gaacagagct agagaatggc atctacgctg ctgattatga aaacccctat | 180 |
| tacgataaca gtaccttcgc ttctcacttt tacgatccag acaacggaaa gacatatatc | 240 |

```
ccattcgcca agcaagctaa ggagactgga gctaagtact tcaagttggc tggagagtca        300
tacaagaata aagacatgaa gcaggccttc ttttatcttg ggttgtcatt gcattatttg        360
ggcgatgtca accaacctat gcatgccgca aactttacga acctgtccta tccacagggt        420
tttcactcca gtacgagaaa ctttgtcgat actattaaag acaactacaa agttaccgat        480
gggaacggat attggaattg gaaaggcacc aaccctgaag aatggattca cggtgcagca        540
gtagttgcaa acaggacta ctctggaatt gtcaatgaca ataccaaaga ttggtttgtg         600
aaagccgcag tctcccagga atatgcagat aaatggagag ctgaagttac acctatgact       660
ggtaaacgac taatggatgc ccaaagagtt actgctggtt acattcaatt atggttcgac       720
acttacggtg acaggtaa                                                     738
```

<210> SEQ ID NO 6
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of the mutant PLC-R20H

<400> SEQUENCE: 6

```
Trp Ser Ala Glu Asp Lys His Lys Glu Gly Val Asn Ser His Leu Trp
1               5                   10                  15

Ile Val Asn His Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Asn Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245
```

<210> SEQ ID NO 7
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of the mutant PLC-N63S

<400> SEQUENCE: 7

```
tggtcagctg aggacaagca taaggaaggt gtgaatagtc acttatggat cgtgaaccgt       60
gccattgata taatgtctag gaatacaact ctggttaagc aagatagagt tgctcaattg      120
aatgaatggc gtacagagct agagaatggc atctacgctg ctgattatga aaacccctat      180
tacgatagca gtaccttcgc ttctcacttt tacgatccag acaacggaaa gacatatatc      240
ccattcgcca agcaagctaa ggagactgga gctaagtact tcaagttggc tggagagtca      300
tacaagaata aagacatgaa gcaggccttc ttttatcttg ggttgtcatt gcattatttg      360
ggcgatgtca accaacctat gcatgccgca aactttacga acctgtccta tccacagggt      420
tttcactcca gtacgagaaa ctttgtcgat actattaaag acaactacaa agttaccgat      480
gggaacggat attggaattg aaaggcacc aaccctgaag aatggattca cggtgcagca      540
gtagttgcaa acaggactactctggaatt gtcaatgaca ataccaaaga ttggtttgtg      600
aaagccgcag tctcccagga atatgcagat aaatggagag ctgaagttac acctatgact      660
ggtaaacgac taatggatgc ccaaagagtt actgctggtt acattcaatt atggttcgac      720
acttacggtg acaggtaa                                                    738
```

<210> SEQ ID NO 8
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of the mutant PLC-N63S

<400> SEQUENCE: 8

```
Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Ser Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140
```

```
Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
            165                 170                 175

His Gly Ala Ala Val Val Ala Lys Gln Asp Tyr Ser Gly Ile Val Asn
        180                 185                 190

Asp Asn Thr Lys Asp Trp Phe Val Lys Ala Ala Val Ser Gln Glu Tyr
            195                 200                 205

Ala Asp Lys Trp Arg Ala Glu Val Thr Pro Met Thr Gly Lys Arg Leu
        210                 215                 220

Met Asp Ala Gln Arg Val Thr Ala Gly Tyr Ile Gln Leu Trp Phe Asp
225                 230                 235                 240

Thr Tyr Gly Asp Arg
            245

<210> SEQ ID NO 9
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of the mutant PLC-A83D

<400> SEQUENCE: 9
tggtcagctg aggacaagca taaggaaggt gtgaatagtc acttatggat cgtgaaccgt    60
gccattgata taatgtctag gaatacaact ctggttaagc aagatagagt tgctcaattg   120
aatgaatggc gtacagagct agagaatggc atctacgctg ctgattatga aaacccctat   180
tacgataaca gtaccttcgc ttctcacttt tacgatccag acaacggaaa gacatatatc   240
ccattcgaca gcaagctaa ggagactgga gctaagtact tcaagttggc tggagagtca   300
tacaagaata aagacatgaa gcaggccttc ttttatcttg ggttgtcatt gcattatttg   360
ggcgatgtca accaacctat gcatgccgca aactttacga acctgtccta tccacagggt   420
tttcactcca agtacgagaa ctttgtcgat actattaaag acaactacaa agttaccgat   480
gggaacggat attggaattg gaaaggcacc aaccctgaag aatggattca cggtgcagca   540
gtagttgcaa aacaggacta ctctggaatt gtcaatgaca ataccaaaga ttggtttgtg   600
aaagccgcag tctcccagga atatgcagat aaatggagag ctgaagttac acctatgact   660
ggtaaacgac taatggatgc ccaaagagtt actgctggtt acattcaatt atggttcgac   720
acttacggtg acaggtaa                                                 738

<210> SEQ ID NO 10
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence mutant PLC-A83D

<400> SEQUENCE: 10

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30
```

Lys Gln Asp Arg Val Ala Gln Leu Asn Glu Trp Arg Thr Glu Leu Glu
            35                  40                  45

Asn Gly Ile Tyr Ala Ala Asp Tyr Glu Asn Pro Tyr Tyr Asp Asn Ser
        50                  55                  60

Thr Phe Ala Ser His Phe Tyr Asp Pro Asp Asn Gly Lys Thr Tyr Ile
65                  70                  75                  80

Pro Phe Asp Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
            115                 120                 125

Ala Ala Asn Phe Thr Asn Leu Ser Tyr Pro Gln Gly Phe His Ser Lys
        130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
210                 215                 220

Met Asp Ala Gln Arg Val Thr Ala Gly Tyr Ile Gln Leu Trp Phe Asp
225                 230                 235                 240

Thr Tyr Gly Asp Arg
            245

<210> SEQ ID NO 11
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-R20HN63SA83D

<400> SEQUENCE: 11
tggtcagctg aggacaagca taaggaaggt gtgaatagtc acttatggat cgtgaaccat      60
gccattgata taatgtctag gaatacaact ctggttaagc aagatagagt tgctcaattg     120
aatgaatggc gaacagagct agagaatggc atctacgctg ctgattatga aaacccctat     180
tacgatagca gtaccttcgc ttctcacttt tacgatccag acaacggaaa gacatatatc     240
ccattcgaca agcaagctaa ggagactgga gctaagtact tcaagttggc tggagagtca     300
tacaagaata agacatgaa gcaggccttc ttttatcttg gttgtcatt gcattatttg      360 ggcgatgtca accaacctat gcatgccgca aactttacga acctgtccta tccacagggt     420
tttcactcca gtacgagaa cttcgtcgat actattaaag acaactacaa agttaccgat     480
gggaacggat attggaattg gaaaggcacc aaccctgagg aatggattca cggtgcagca     540
gtagtcgcaa acaggacta ctctggaatt gtcaatgaca ataccaaaga ttggtttgtg     600
aaagccgcag tctcccagga atatgcagat aaatggagag ctgaagttac acctatgact     660
ggtaaacgac taatggatgc ccaaagagtt actgctggtt acattcaatt atggttcgac     720
acttacggtg acaggtaa                                                       738

<210> SEQ ID NO 12
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence PLC-R20HN63SA83D

<400> SEQUENCE: 12

```
Trp Ser Ala Glu Asp Lys His Lys Glu Gly Val Asn Ser His Leu Trp
 1               5                  10                  15

Ile Val Asn His Ala Ile Asp Ile Met Ser Arg Asn Thr Thr Leu Val
                20                  25                  30

Lys Gln Asp Arg Val Ala Gln Leu Asn Glu Trp Arg Thr Glu Leu Glu
            35                  40                  45

Asn Gly Ile Tyr Ala Ala Asp Tyr Glu Asn Pro Tyr Tyr Asp Ser Ser
        50                  55                  60

Thr Phe Ala Ser His Phe Tyr Asp Pro Asp Asn Gly Lys Thr Tyr Ile
65                  70                  75                  80

Pro Phe Asp Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245
```

<210> SEQ ID NO 13
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63A

<400> SEQUENCE: 13
tggtcagctg aggacaagca taaggaaggt gtgaatagtc acttatggat cgtgaaccgt      60

-continued

```
gccattgata taatgtctag aatacaact ctggttaagc aagatagagt tgctcaattg    120
aatgaatggc gtacagagct agagaatggc atctacgctg ctgattatga aaaccctat    180 tacgatgcca gtaccttcgc ttctcacttt tacgatccag acaacggaaa gacatatatc    240
ccattcgcca agcaagctaa ggagactgga gctaagtact tcaagttggc tggagagtca    300
tacaagaata agacatgaa gcaggccttc ttttatcttg ggttgtcatt gcattatttg    360
ggcgatgtca accaacctat gcatgccgca aactttacga acctgtccta tccacagggt    420
tttcactcca gtacgagaa ctttgtcgat actattaaag acaactacaa agttaccgat    480
gggaacggat attggaattg gaaaggcacc aaccctgaag aatggattca cggtgcagca    540
gtagttgcaa acaggacta ctctggaatt gtcaatgaca ataccaaaga ttggtttgtg    600
aaagccgcag tctcccagga atatgcagat aaatggagag ctgaagttac acctatgact    660
ggtaaacgac taatggatgc ccaaagagtt actgctggtt acattcaatt atggttcgac    720
acttacggtg acaggtaa                                                  738
```

<210> SEQ ID NO 14
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence PLC-N63A

<400> SEQUENCE: 14

```
Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Ala Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220
```

Met Asp Ala Gln Arg Val Thr Ala Gly Tyr Ile Gln Leu Trp Phe Asp
225                 230                 235                 240

Thr Tyr Gly Asp Arg
            245

<210> SEQ ID NO 15
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63C

<400> SEQUENCE: 15

```
tggtcagctg aggacaagca taaggaaggt gtgaatagtc acttatggat cgtgaaccgt      60
gccattgata taatgtctag aatacaact ctggttaagc aagatagagt tgctcaattg     120
aatgaatggc gtacagagct agagaatggc atctacgctg ctgattatga aaacccctat     180
tacgattgca gtaccttcgc ttctcacttt tacgatccag acaacggaaa gacatatatc     240
ccattcgcca agcaagctaa ggagactgga gctaagtact tcaagttggc tggagagtca     300
tacaagaata agacatgaa gcaggccttc ttttatcttg ggttgtcatt gcattatttg     360
ggcgatgtca accaacctat gcatgccgca aactttacga acctgtccta tccacagggt     420
tttcactcca agtacgagaa ctttgtcgat actattaaag acaactacaa agttaccgat     480
gggaacggat attggaattg aaaggcacc aaccctgaag aatggattca cggtgcagca     540
gtagttgcaa acaggacta ctctggaatt gtcaatgaca ataccaaaga ttggtttgtg     600
aaagccgcag tctcccagga atatgcagat aaatggagag ctgaagttac acctatgact     660
ggtaaacgac taatggatgc ccaaagagtt actgctggtt acattcaatt atggttcgac     720
acttacggtg acaggtaa                                                   738
```

<210> SEQ ID NO 16
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63C

<400> SEQUENCE: 16

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Cys Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
115                 120                 125

Ala Ala Asn Phe Thr Asn Leu Ser Tyr Pro Gln Gly Phe His Ser Lys
130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
210                 215                 220

Met Asp Ala Gln Arg Val Thr Ala Gly Tyr Ile Gln Leu Trp Phe Asp
225                 230                 235                 240

Thr Tyr Gly Asp Arg
            245

<210> SEQ ID NO 17
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63D

<400> SEQUENCE: 17
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaacccctat     180
tacgatgaca gtaccttcgc ttctcacttt tacgatccag acaacggaaa gacatatatc     240
ccattcgcca agcaagctaa ggagactgga gctaagtact tcaagttggc tggagagtca     300
tacaagaata aagacatgaa gcaggccttc ttttatcttg ggttgtcatt gcattatttg     360
ggcgatgtca accaacctat gcatgccgca aactttacga acctgtccta tccacagggt     420
tttcactcca agtacgagaa cttgtcgat actattaaag acaactacaa agttaccgat     480
gggaacggat attggaattg gaaaggcacc aaccctgaag aatggattca cggtgcagca     540
gtagttgcaa acaggactac tctctggaatt gtcaatgaca ataccaaaga ttggtttgtg     600
aaagccgcag tctcccagga atatgcagat aaatggagag ctgaagttac acctatgact     660
ggtaaacgac taatggatgc ccaaagagtt actgctggtt acattcaatt atggttcgac     720
acttacggtg acaggtaa                                                    738

<210> SEQ ID NO 18
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63D

<400> SEQUENCE: 18

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Asp Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245

<210> SEQ ID NO 19
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63E

<400> SEQUENCE: 19
tggtcagctg aggacaagca taaggaaggt gtgaatagtc acttatggat cgtgaaccgt     60
gccattgata taatgtctag gaatacaact ctggttaagc aagatagagt tgctcaattg    120
aatgaatggc gtacagagct agagaatggc atctacgctg ctgattatga aaaccccctat  180 tacgatgaga gtaccttcgc ttctcacttt tacgatccag acaacggaaa gacatatatc    240
ccattcgcca agcaagctaa ggagactgga gctaagtact tcaagttggc tggagagtca    300
tacaagaata agacatgaa gcaggccttc ttttatcttg gttgtcatt gcattatttg      360 ggcgatgtca accaacctat gcatgccgca aactttacga acctgtccta tccacagggt   420
tttcactcca gtacgagaa ctttgtcgat actattaaag acaactacaa agttaccgat    480
gggaacggat attggaattg gaaaggcacc aaccctgaag aatggattca cggtgcagca   540

```
gtagttgcaa acaggactc ctctggaatt gtcaatgaca ataccaaaga ttggtttgtg      600
aaagccgcag tctcccagga atatgcagat aaatggagag ctgaagttac acctatgact      660
ggtaaacgac taatggatgc ccaaagagtt actgctggtt acattcaatt atggttcgac      720
acttacggtg acaggtaa                                                    738
```

```
<210> SEQ ID NO 20
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63E
```

<400> SEQUENCE: 20

| Trp | Ser | Ala | Glu | Asp | Lys | His | Lys | Glu | Gly | Val | Asn | Ser | His | Leu | Trp |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |

| Ile | Val | Asn | Arg | Ala | Ile | Asp | Ile | Met | Ser | Arg | Asn | Thr | Thr | Leu | Val |
|     |     |     | 20  |     |     |     |     | 25  |     |     |     |     | 30  |     |     |

| Lys | Gln | Asp | Arg | Val | Ala | Gln | Leu | Asn | Glu | Trp | Arg | Thr | Glu | Leu | Glu |
|     |     |     | 35  |     |     |     |     | 40  |     |     |     |     | 45  |     |     |

| Asn | Gly | Ile | Tyr | Ala | Ala | Asp | Tyr | Glu | Asn | Pro | Tyr | Tyr | Asp | Glu | Ser |
|     |     | 50  |     |     |     |     | 55  |     |     |     |     | 60  |     |     |     |

| Thr | Phe | Ala | Ser | His | Phe | Tyr | Asp | Pro | Asp | Asn | Gly | Lys | Thr | Tyr | Ile |
| 65  |     |     |     |     | 70  |     |     |     |     | 75  |     |     |     |     | 80  |

| Pro | Phe | Ala | Lys | Gln | Ala | Lys | Glu | Thr | Gly | Ala | Lys | Tyr | Phe | Lys | Leu |
|     |     |     |     | 85  |     |     |     |     | 90  |     |     |     |     | 95  |     |

| Ala | Gly | Glu | Ser | Tyr | Lys | Asn | Lys | Asp | Met | Lys | Gln | Ala | Phe | Phe | Tyr |
|     |     |     |     | 100 |     |     |     |     | 105 |     |     |     |     | 110 |     |

| Leu | Gly | Leu | Ser | Leu | His | Tyr | Leu | Gly | Asp | Val | Asn | Gln | Pro | Met | His |
|     |     |     |     | 115 |     |     |     |     | 120 |     |     |     |     | 125 |     |

| Ala | Ala | Asn | Phe | Thr | Asn | Leu | Ser | Tyr | Pro | Gln | Gly | Phe | His | Ser | Lys |
|     |     |     | 130 |     |     |     |     | 135 |     |     |     |     | 140 |     |     |

| Tyr | Glu | Asn | Phe | Val | Asp | Thr | Ile | Lys | Asp | Asn | Tyr | Lys | Val | Thr | Asp |
| 145 |     |     |     |     | 150 |     |     |     |     | 155 |     |     |     |     | 160 |

| Gly | Asn | Gly | Tyr | Trp | Asn | Trp | Lys | Gly | Thr | Asn | Pro | Glu | Glu | Trp | Ile |
|     |     |     |     | 165 |     |     |     |     | 170 |     |     |     |     | 175 |     |

| His | Gly | Ala | Ala | Val | Val | Ala | Lys | Gln | Asp | Tyr | Ser | Gly | Ile | Val | Asn |
|     |     |     | 180 |     |     |     |     | 185 |     |     |     |     | 190 |     |     |

| Asp | Asn | Thr | Lys | Asp | Trp | Phe | Val | Lys | Ala | Ala | Val | Ser | Gln | Glu | Tyr |
|     |     |     | 195 |     |     |     |     | 200 |     |     |     |     | 205 |     |     |

| Ala | Asp | Lys | Trp | Arg | Ala | Glu | Val | Thr | Pro | Met | Thr | Gly | Lys | Arg | Leu |
|     | 210 |     |     |     |     | 215 |     |     |     |     | 220 |     |     |     |     |

| Met | Asp | Ala | Gln | Arg | Val | Thr | Ala | Gly | Tyr | Ile | Gln | Leu | Trp | Phe | Asp |
| 225 |     |     |     |     | 230 |     |     |     |     | 235 |     |     |     |     | 240 |

| Thr | Tyr | Gly | Asp | Arg |
|     |     |     |     | 245 |

```
<210> SEQ ID NO 21
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63F
```

<400> SEQUENCE: 21

```
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaaccccctat   180
tacgatttca gtaccttcgc ttctcacttt tacgatccag acaacggaaa gacatatatc    240
ccattcgcca agcaagctaa ggagactgga gctaagtact tcaagttggc tggagagtca    300
tacaagaata agacatgaa gcaggccttc ttttatcttg ggttgtcatt gcattatttg     360
ggcgatgtca accaacctat gcatgccgca aactttacga acctgtccta tccacagggt    420
tttcactcca gtacgagaa ctttgtcgat actattaaag acaactacaa agttaccgat     480
gggaacggat attggaattg aaaggcacc aaccctgaag aatggattca cggtgcagca     540
gtagttgcaa acaggacta ctctggaatt gtcaatgaca ataccaaaga ttggtttgtg     600
aaagccgcag tctcccagga atatgcagat aaatggagag ctgaagttac acctatgact    660
ggtaaacgac taatggatgc ccaaagagtt actgctggtt acattcaatt atggttcgac    720
acttacggtg acaggtaa                                                    738
```

<210> SEQ ID NO 22
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63F

<400> SEQUENCE: 22

```
Trp Ser Ala Glu Asp Lys His Lys Glu Gly Val Asn Ser His Leu Trp
  1               5                  10                  15
Ile Val Asn Arg Ala Ile Asp Ile Met Ser Arg Asn Thr Thr Leu Val
             20                  25                  30
Lys Gln Asp Arg Val Ala Gln Leu Asn Glu Trp Arg Thr Glu Leu Glu
         35                  40                  45
Asn Gly Ile Tyr Ala Ala Asp Tyr Glu Asn Pro Tyr Tyr Asp Phe Ser
     50                  55                  60
Thr Phe Ala Ser His Phe Tyr Asp Pro Asp Asn Gly Lys Thr Tyr Ile
 65                  70                  75                  80
Pro Phe Ala Lys Gln Ala Lys Glu Thr Gly Ala Lys Tyr Phe Lys Leu
                 85                  90                  95
Ala Gly Glu Ser Tyr Lys Asn Lys Asp Met Lys Gln Ala Phe Phe Tyr
            100                 105                 110
Leu Gly Leu Ser Leu His Tyr Leu Gly Asp Val Asn Gln Pro Met His
        115                 120                 125
Ala Ala Asn Phe Thr Asn Leu Ser Tyr Pro Gln Gly Phe His Ser Lys
    130                 135                 140
Tyr Glu Asn Phe Val Asp Thr Ile Lys Asp Asn Tyr Lys Val Thr Asp
145                 150                 155                 160
Gly Asn Gly Tyr Trp Asn Trp Lys Gly Thr Asn Pro Glu Glu Trp Ile
                165                 170                 175
His Gly Ala Ala Val Val Ala Lys Gln Asp Tyr Ser Gly Ile Val Asn
            180                 185                 190
Asp Asn Thr Lys Asp Trp Phe Val Lys Ala Ala Val Ser Gln Glu Tyr
```

```
            195                 200                 205
Ala Asp Lys Trp Arg Ala Glu Val Thr Pro Met Thr Gly Lys Arg Leu
            210                 215                 220

Met Asp Ala Gln Arg Val Thr Ala Gly Tyr Ile Gln Leu Trp Phe Asp
225                 230                 235                 240

Thr Tyr Gly Asp Arg
            245

<210> SEQ ID NO 23
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63G

<400> SEQUENCE: 23
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaaccccctat    180 tacgatgaga gtaccttcgc ttctcacttt tacgatccag acaacggaaa gacatatatc     240
ccattcgcca agcaagctaa ggagactgga gctaagtact caagttggc tggagagtca      300 tacaagaata agacatgaa gcaggccttc ttttatcttg ggttgtcatt gcattatttg      360
ggcgatgtca accaacctat gcatgccgca aactttacga acctgtccta tccacagggt     420
tttcactcca gtacgagaa cctttgtcgat actattaaag acaactacaa agttaccgat    480
gggaacggat attggaattg gaaaggcacc aaccctgaag aatggattca cggtgcagca     540
gtagttgcaa acaggacta ctctggaatt gtcaatgaca ataccaaaga ttggtttgtg     600
aaagccgcag tctcccagga atatgcagat aaatggagag ctgaagttac acctatgact     660
ggtaaacgac taatggatgc ccaaagagtt actgctggtt acattcaatt atggttcgac    720
acttacggtg acaggtaa                                                   738

<210> SEQ ID NO 24
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63G

<400> SEQUENCE: 24

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Gly Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
```

```
            85                  90                  95
Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
            115                 120                 125

Ala Ala Asn Phe Thr Asn Leu Ser Tyr Pro Gln Gly Phe His Ser Lys
            130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
                180                 185                 190

Asp Asn Thr Lys Asp Trp Phe Val Lys Ala Ala Val Ser Gln Glu Tyr
                195                 200                 205

Ala Asp Lys Trp Arg Ala Glu Val Thr Pro Met Thr Gly Lys Arg Leu
            210                 215                 220

Met Asp Ala Gln Arg Val Thr Ala Gly Tyr Ile Gln Leu Trp Phe Asp
225                 230                 235                 240

Thr Tyr Gly Asp Arg
            245
```

<210> SEQ ID NO 25
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63H

<400> SEQUENCE: 25

```
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaacccctat     180
tacgatcaca gtaccttcgc ttctcacttt tacgatccag acaacggaaa gacatatatc     240
ccattcgcca agcaagctaa ggagactgga gctaagtact tcaagttggc tggagagtca     300
tacaagaata agacatgaa gcaggccttc tttatcttg ggttgtcatt gcattatttg       360
ggcgatgtca accaacctat gcatgccgca aactttacga acctgtccta tccacagggt     420
tttcactcca agtacgagaa ctttgtcgat actattaaag acaactacaa agttaccgat     480
gggaacggat attggaattg gaaaggcacc aaccctgaag aatggattca cggtgcagca     540
gtagttgcaa acaggactac ctctggaatt gtcaatgaca ataccaaaga ttggtttgtg     600
aaagccgcag tctcccagga atatgcagat aaatggagag ctgaagttac acctatgact     660
ggtaaacgac taatggatgc ccaaagagtt actgctggtt acattcaatt atggttcgac     720
acttacggtg acaggtaa                                                   738
```

<210> SEQ ID NO 26
<211> LENGTH: 245
<212> TYPE: PRT
<213> ORGANISM: Artificial Sequence
<220> FEATURE:
<223> OTHER INFORMATION: fusion protein
<220> FEATURE:

<221> NAME/KEY: MISC_FEATURE
<223> OTHER INFORMATION: the amino acid sequence of PLC-N63H

<400> SEQUENCE: 26

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp His Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245

<210> SEQ ID NO 27
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63I

<400> SEQUENCE: 27
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaaccctat     180 tacgatatca gtaccttcgc ttctcacttt tacgatccag acaacggaaa gacatatatc     240
ccattcgcca agcaagctaa ggagactgga gctaagtact tcaagttggc tggagagtca     300
tacaagaata agacatgaa gcaggccttc ttttatcttg gttgtcatt gcattatttg     360 ggcgatgtca accaacctat gcatgccgca aactttacga acctgtccta tccacagggt     420

```
tttcactcca agtacgagaa ctttgtcgat actattaaag acaactacaa agttaccgat    480
gggaacggat attggaattg aaaggcacc aaccctgaaa atggattca cggtgcagca     540 gtagttgcaa aacaggacta ctctggaatt gtcaatgaca ataccaaaga ttggtttgtg    600
aaagccgcag tctcccagga atatgcagat aaatggagag ctgaagttac acctatgact    660
ggtaaacgac taatggatgc ccaaagagtt actgctggtt acattcaatt atggttcgac    720
acttacggtg acaggtaa                                                  738
```

<210> SEQ ID NO 28
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63I

<400> SEQUENCE: 28

```
Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
                20                  25                  30

Lys Gln Asp Arg Val Ala Gln Leu Asn Glu Trp Arg Thr Glu Leu Glu
            35                  40                  45

Asn Gly Ile Tyr Ala Ala Asp Tyr Glu Asn Pro Tyr Tyr Asp Ile Ser
        50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245
```

<210> SEQ ID NO 29
<211> LENGTH: 738
<212> TYPE: DNA
<213> ORGANISM: Artificial Sequence

```
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63K

<400> SEQUENCE: 29
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaacccctat     180
tacgataaga gtaccttcgc ttctcacttt tacgatccag acaacggaaa gacatatatc     240
ccattcgcca agcaagctaa ggagactgga gctaagtact tcaagttggc tggagagtca     300
tacaagaata aagacatgaa gcaggccttc ttttatcttg ggttgtcatt gcattatttg     360
ggcgatgtca accaacctat gcatgccgca aactttacga acctgtccta tccacagggt     420
tttcactcca gtacgagaa  ctttgtcgat actattaaag acaactacaa agttaccgat     480
gggaacggat attggaattg gaaaggcacc aaccctgaag aatggattca cggtgcagca     540
gtagttgcaa acaggactac ctctggaatt gtcaatgaca ataccaaaga ttggtttgtg     600
aaagccgcag tctcccagga atatgcagat aaatggagag ctgaagttac acctatgact     660
ggtaaacgac taatggatgc ccaaagagtt actgctggtt acattcaatt atggttcgac     720
acttacggtg acaggtaa                                                   738

<210> SEQ ID NO 30
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63K

<400> SEQUENCE: 30

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Lys Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175
```

His Gly Ala Ala Val Ala Lys Gln Asp Tyr Ser Gly Ile Val Asn
        180                 185                 190

Asp Asn Thr Lys Asp Trp Phe Val Lys Ala Ala Val Ser Gln Glu Tyr
            195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
            245

<210> SEQ ID NO 31
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63L

<400> SEQUENCE: 31
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaacccctat     180
tacgatttga gtaccttcgc ttctcacttt tacgatccag acaacggaaa gacatatatc     240
ccattcgcca agcaagctaa ggagactgga gctaagtact tcaagttggc tggagagtca     300
tacaagaata aagacatgaa gcaggccttc ttttatcttg ggttgtcatt gcattatttg     360
ggcgatgtca accaacctat gcatgccgca aactttacga acctgtccta tccacagggt     420
tttcactcca gtacgagaa cttttgtcgat actattaaag acaactacaa agttaccgat     480
gggaacggat attggaattg aaaggcacc aaccctgaag aatggattca cggtgcagca     540
gtagttgcaa acaggactac tctctggaatt gtcaatgaca ataccaaaga ttggtttgtg     600
aaagccgcag tctcccagga aatatgcagat aaatggagag ctgaagttac acctatgact     660
ggtaaacgac taatggatgc ccaaagagtt actgctggtt acattcaatt atggttcgac     720
acttacggtg acaggtaa                                                    738

<210> SEQ ID NO 32
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63L

<400> SEQUENCE: 32

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Leu Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245

<210> SEQ ID NO 33
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63M

<400> SEQUENCE: 33
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaacccctat     180
tacgatatga gtaccttcgc ttctcacttt tacgatccag acaacggaaa gacatatatc     240
ccattcgcca agcaagctaa ggagactgga gctaagtact caagttggc tggagagtca      300 tacaagaata agacatgaa gcaggccttc ttttatcttg ggttgtcatt gcattatttg      360
ggcgatgtca accaacctat gcatgccgca aactttacga acctgtccta tccacagggt     420
tttcactcca gtacgagaa ctttgtcgat actattaaag acaactacaa agttaccgat      480
gggaacggat attggaattg gaaaggcacc aaccctgaag aatggattca cggtgcagca     540
gtagttgcaa acaggacta ctctggaatt gtcaatgaca ataccaaaga ttggtttgtg      600
aaagccgcag tctcccagga atatgcagat aaatggagag ctgaagttac acctatgact     660
ggtaaacgac taatggatgc ccaaagagtt actgctggtt acattcaatt atggttcgac     720
acttacggtg acaggtaa                                                   738

<210> SEQ ID NO 34
<211> LENGTH: 245

<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63M

<400> SEQUENCE: 34

```
Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Met Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245
```

<210> SEQ ID NO 35
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63P

<400> SEQUENCE: 35

```
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaaccccta     180 tacgatccaa gtaccttcgc ttctcacttt tacgatccag acaacggaaa gacatatatc     240
```

```
ccattcgcca agcaagctaa ggagactgga gctaagtact tcaagttggc tggagagtca      300
tacaagaata aagacatgaa gcaggccttc ttttatcttg ggttgtcatt gcattatttg      360
ggcgatgtca accaacctat gcatgccgca aactttacga acctgtccta tccacagggt      420
tttcactcca agtacgagaa ctttgtcgat actattaaag acaactacaa agttaccgat      480
gggaacggat attggaattg aaaggcacc aaccctgaag aatggattca cggtgcagca       540
gtagttgcaa acaggacta ctctggaatt gtcaatgaca ataccaaaga ttggtttgtg       600
aaagccgcag tctcccagga atatgcagat aaatggagag ctgaagttac acctatgact      660
ggtaaacgac taatggatgc ccaaagagtt actgctggtt acattcaatt atggttcgac      720
acttacggtg acaggtaa                                                    738
```

<210> SEQ ID NO 36
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63P

<400> SEQUENCE: 36

```
Trp Ser Ala Glu Asp Lys His Lys Glu Gly Val Asn Ser His Leu Trp
  1               5                  10                  15

Ile Val Asn Arg Ala Ile Asp Ile Met Ser Arg Asn Thr Thr Leu Val
                 20                  25                  30

Lys Gln Asp Arg Val Ala Gln Leu Asn Glu Trp Arg Thr Glu Leu Glu
             35                  40                  45

Asn Gly Ile Tyr Ala Ala Asp Tyr Glu Asn Pro Tyr Tyr Asp Pro Ser
         50                  55                  60

Thr Phe Ala Ser His Phe Tyr Asp Pro Asp Asn Gly Lys Thr Tyr Ile
 65                  70                  75                  80

Pro Phe Ala Lys Gln Ala Lys Glu Thr Gly Ala Lys Tyr Phe Lys Leu
                 85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245
```

<210> SEQ ID NO 37
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63Q

<400> SEQUENCE: 37

```
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaaccccctat    180 tacgatcaaa gtaccttcgc ttctcacttt tacgatccag acaacggaaa gacatatatc    240
ccattcgcca agcaagctaa ggagactgga gctaagtact tcaagttggc tggagagtca    300
tacaagaata agacatgaa gcaggccttc ttttatcttg ggttgtcatt gcattatttg     360
ggcgatgtca accaacctat gcatgccgca aactttacga acctgtccta tccacagggt    420
tttcactcca gtacgagaa ctttgtcgat actattaaag acaactacaa agttaccgat    480
gggaacggat attggaattg aaaggcacc aaccctgaag aatggattca cggtgcagca     540
gtagttgcaa acaggacta ctctggaatt gtcaatgaca ataccaaaga ttggtttgtg     600
aaagccgcag tctcccagga atatgcagat aaatggagag ctgaagttac acctatgact    660
ggtaaacgac taatggatgc ccaaagagtt actgctggtt acattcaatt atggttcgac    720
acttacggtg acaggtaa                                                   738
```

<210> SEQ ID NO 38
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63Q

<400> SEQUENCE: 38

```
Trp Ser Ala Glu Asp Lys His Lys Glu Gly Val Asn Ser His Leu Trp
  1               5                  10                  15

Ile Val Asn Arg Ala Ile Asp Ile Met Ser Arg Asn Thr Thr Leu Val
             20                  25                  30

Lys Gln Asp Arg Val Ala Gln Leu Asn Glu Trp Arg Thr Glu Leu Glu
         35                  40                  45

Asn Gly Ile Tyr Ala Ala Asp Tyr Glu Asn Pro Tyr Tyr Asp Gln Ser
     50                  55                  60

Thr Phe Ala Ser His Phe Tyr Asp Pro Asp Asn Gly Lys Thr Tyr Ile
 65                  70                  75                  80

Pro Phe Ala Lys Gln Ala Lys Glu Thr Gly Ala Lys Tyr Phe Lys Leu
                 85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140
```

```
Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
                195                 200                 205

Ala Asp Lys Trp Arg Ala Glu Val Thr Pro Met Thr Gly Lys Arg Leu
        210                 215                 220

Met Asp Ala Gln Arg Val Thr Ala Gly Tyr Ile Gln Leu Trp Phe Asp
225                 230                 235                 240

Thr Tyr Gly Asp Arg
                245

<210> SEQ ID NO 39
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63R

<400> SEQUENCE: 39
tggtcagctg aggacaagca taaggaaggt gtgaatagtc acttatggat cgtgaaccgt     60
gccattgata taatgtctag gaatacaact ctggttaagc aagatagagt tgctcaattg    120
aatgaatggc gtacagagct agagaatggc atctacgctg ctgattatga aaacccctat    180
tacgataaga gtaccttcgc ttctcacttt tacgatccag acaacggaaa gacatatatc    240
ccattcgcca agcaagctaa ggagactgga gctaagtact tcaagttggc tggagagtca    300
tacaagaata agacatgaa gcaggccttc ttttatcttg ggttgtcatt gcattatttg    360
ggcgatgtca accaacctat gcatgccgca aactttacga acctgtccta tccacagggt    420
tttcactcca gtacgagaa cttttgtcgat actattaaag acaactacaa agttaccgat    480
gggaacggat attggaattg aaaggcacc aaccctgaag aatggattca cggtgcagca    540
gtagttgcaa acaggacta ctctggaatt gtcaatgaca ataccaaaga ttggtttgtg    600
aaagccgcag tctcccagga atatgcagat aaatggagag ctgaagttac acctatgact    660
ggtaaacgac taatggatgc ccaaagagtt actgctggtt acattcaatt atggttcgac    720
acttacggtg acaggtaa                                                 738

<210> SEQ ID NO 40
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63R

<400> SEQUENCE: 40

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30
```

-continued

```
Lys Gln Asp Arg Val Ala Gln Leu Asn Glu Trp Arg Thr Glu Leu Glu
         35                  40                  45

Asn Gly Ile Tyr Ala Ala Asp Tyr Glu Asn Pro Tyr Tyr Asp Arg Ser
 50                  55                  60

Thr Phe Ala Ser His Phe Tyr Asp Pro Asp Asn Gly Lys Thr Tyr Ile
 65                  70                  75                  80

Pro Phe Ala Lys Gln Ala Lys Glu Thr Gly Ala Lys Tyr Phe Lys Leu
                 85                  90                  95

Ala Gly Glu Ser Tyr Lys Asn Lys Asp Met Lys Gln Ala Phe Phe Tyr
                100                 105                 110

Leu Gly Leu Ser Leu His Tyr Leu Gly Asp Val Asn Gln Pro Met His
            115                 120                 125

Ala Ala Asn Phe Thr Asn Leu Ser Tyr Pro Gln Gly Phe His Ser Lys
130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245
```

<210> SEQ ID NO 41
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63T

<400> SEQUENCE: 41

```
tggtcagctg aggacaagca taaggaaggt gtgaatagtc acttatggat cgtgaaccgt    60
gccattgata taatgtctag gaatacaact ctggttaagc aagatagagt tgctcaattg   120
aatgaatggc gtacagagct agagaatggc atctacgctg ctgattatga aaacccctat   180
tacgatacca gtaccttcgc ttctcacttt tacgatccag acaacggaaa gacatatatc   240
ccattcgcca agcaagctaa ggagactgga gctaagtact caagttggc tggagagtca   300
tacaagaata agacatgaa gcaggccttc ttttatcttg gttgtcatt gcattatttg   360
ggcgatgtca accaacctat gcatgccgca aactttacga acctgtccta tccacagggt   420
tttcactcca gtacgagaa ctttgtcgat actattaaag acaactacaa agttaccgat   480
gggaacggat attggaattg aaaggcacc aaccctgaag aatggattca cggtgcagca   540
gtagttgcaa acaggacta ctctggaatt gtcaatgaca ataccaaaga ttggtttgtg   600
aaagccgcag tctcccagga atatgcagat aaatggagag ctgaagttac acctatgact   660
ggtaaacgac taatggatgc ccaaagagtt actgctggtt acattcaatt atggttcgac   720
```
acttacggtg acaggtaa                                                       738

<210> SEQ ID NO 42
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63T

<400> SEQUENCE: 42

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Thr Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245

<210> SEQ ID NO 43
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63V

<400> SEQUENCE: 43
tggtcagctg aggacaagca taaggaaggt gtgaatagtc acttatggat cgtgaaccgt     60
gccattgata taatgtctag gaatacaact ctggttaagc aagatagagt tgctcaattg    120

-continued

```
aatgaatggc gtacagagct agagaatggc atctacgctg ctgattatga aaaccccta t       180 tacgatgtca gtaccttcgc ttctcacttt tacgatccag acaacggaaa gacatatatc       240
ccattcgcca agcaagctaa ggagactgga gctaagtact tcaagttggc tggagagtca       300
tacaagaata aagacatgaa gcaggccttc ttttatcttg ggttgtcatt gcattatttg       360
ggcgatgtca accaacctat gcatgccgca aactttacga acctgtccta tccacagggt       420
tttcactcca gtacgagaaa cttt gtcgat actattaaag acaactacaa agttaccgat       480
gggaacggat attggaattg gaaaggcacc aaccctgaag aatggattca cggtgcagca       540
gtagttgcaa acaggacta ctctggaatt gtcaatgaca ataccaaaga ttggtttgtg       600
aaagccgcag tctcccagga atatgcagat aaatggagag ctgaagttac acctatgact       660
ggtaaacgac taatggatgc ccaaagagtt actgctggtt acattcaatt atggttcgac       720
acttacggtg acaggtaa                                                      738
```

<210> SEQ ID NO 44
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63V

<400> SEQUENCE: 44

```
Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Val Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
```

225              230              235              240

Thr Tyr Gly Asp Arg
              245

<210> SEQ ID NO 45
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63W

<400> SEQUENCE: 45
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaacccctat     180
tacgattgga gtaccttcgc ttctcacttt tacgatccag acaacggaaa gacatatatc     240
ccattcgcca agcaagctaa ggagactgga gctaagtact tcaagttggc tggagagtca     300
tacaagaata agacatgaa gcaggccttc ttttatcttg gttgtcatt gcattatttg      360 ggcgatgtca accaacctat gcatgccgca aactttacga acctgtccta tccacagggt     420
tttcactcca gtacgagaa ctttgtcgat actattaaag acaactacaa agttaccgat      480
gggaacggat attggaattg aaaggcacc aaccctgaag aatggattca cggtgcagca      540
gtagttgcaa acaggacta ctctggaatt gtcaatgaca ataccaaaga ttggtttgtg      600
aaagccgcag tctcccagga atatgcagat aaatggagag ctgaagttac acctatgact     660
ggtaaacgac taatggatgc ccaaagagtt actgctggtt acattcaatt atggttcgac     720
acttacggtg acaggtaa                                                   738

<210> SEQ ID NO 46
<211> LENGTH: 245
<212> TYPE: PRT
<213> ORGANISM: Artificial Sequence
<220> FEATURE:
<223> OTHER INFORMATION: fusion protein

<400> SEQUENCE: 46

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp Tyr Glu Asn Pro Tyr Tyr Asp Trp Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
            165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
            245

<210> SEQ ID NO 47
<211> LENGTH: 738
<212> TYPE: DNA
<213> ORGANISM: Artificial Sequence
<220> FEATURE:
<223> OTHER INFORMATION: fusion polynucleotide
<220> FEATURE:
<221> NAME/KEY: misc_feature
<223> OTHER INFORMATION: the DNA coding sequence of PLC-N63Y

<400> SEQUENCE: 47
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgattatga aaacccctat     180
tacgattaca gtaccttcgc ttctcacttt tacgatccag acaacggaaa gacatatatc     240
ccattcgcca agcaagctaa ggagactgga gctaagtact tcaagttggc tggagagtca     300
tacaagaata agacatgaa gcaggccttc ttttatcttg ggttgtcatt gcattatttg     360
ggcgatgtca accaacctat gcatgccgca aactttacga acctgtccta tccacagggt     420
tttcactcca agtacgagaa ctttgtcgat actattaaag acaactacaa agttaccgat     480
gggaacggat attggaattg gaaaggcacc aaccctgaag aatggattca cggtgcagca     540
gtagttgcaa acaggacta ctctggaatt gtcaatgaca ataccaaaga ttggtttgtg     600
aaagccgcag tctcccagga atatgcagat aaatggagag ctgaagttac acctatgact     660
ggtaaacgac taatggatgc ccaaagagtt actgctggtt acattcaatt atggttcgac     720
acttacggtg acaggtaa                                                    738

<210> SEQ ID NO 48
<211> LENGTH: 245
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<223> OTHER INFORMATION: the amino acid sequence of PLC-N63Y

<400> SEQUENCE: 48

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val

```
                20                  25                  30
Lys Gln Asp Arg Val Ala Gln Leu Asn Glu Trp Arg Thr Glu Leu Glu
            35                  40                  45

Asn Gly Ile Tyr Ala Ala Asp Tyr Glu Asn Pro Tyr Asp Tyr Ser
        50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245

<210> SEQ ID NO 49
<211> LENGTH: 35
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 49
ccggacgtcg ctagcagatc taacatccaa agacg                              35

<210> SEQ ID NO 50
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 50
tcatcgtttc gcctaggatc cttcgaataa ttagttg                            37

<210> SEQ ID NO 51
<211> LENGTH: 30
<212> TYPE: DNA
<213> ORGANISM: Artificial Sequence
```

```
<220> FEATURE:
<223> OTHER INFORMATION: synthetic
<220> FEATURE:
<221> NAME/KEY: misc_feature
<223> OTHER INFORMATION: Primer

<400> SEQUENCE: 51
gatcctaggc gaaacgatga gatttccttc                                          30

<210> SEQ ID NO 52
<211> LENGTH: 26
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 52
ccggaattct tacctgtcac cgtaag                                              26

<210> SEQ ID NO 53
<211> LENGTH: 35
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 53
gttaaaatca aaacgttgtc aattggaacc agtcg                                    35

<210> SEQ ID NO 54
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 54
ccaattgaca acgttgattt taacgacttt taacgacaac                               40

<210> SEQ ID NO 55
<211> LENGTH: 22
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 55
cgactggttc caattgacaa cg                                                  22

<210> SEQ ID NO 56
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
```

<223> OTHER INFORMATION: Primer

<400> SEQUENCE: 56
ggcaaatggc attctgacat cctc                                           24

<210> SEQ ID NO 57
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 57
cccaagcttg gtcagctgag gac                                            23

<210> SEQ ID NO 58
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 58
ccggaattct tacctgtcac cgta                                           24

<210> SEQ ID NO 59
<211> LENGTH: 33
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 59
tatcaatggc atggttcacg atccataagt gac                                 33

<210> SEQ ID NO 60
<211> LENGTH: 35
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 60
ggatcgtgaa ccatgccatt gatataatgt ctagg                               35

<210> SEQ ID NO 61
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 61
cgaaggtact gctatcgtaa tagggqtttt cataatc          37

<210> SEQ ID NO 62
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 62
ctattacgat agcagtacct tcgcttctca cttttac          37

<210> SEQ ID NO 63
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 63
cttagcttgc ttgtcgaatg ggatatatgt ctttccg          37

<210> SEQ ID NO 64
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 64
atcccattcg acaagcaagc taaggagact g          31

<210> SEQ ID NO 65
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 65
cgaaggtact ggcatcgtaa tagggqtttt cataatc          37

<210> SEQ ID NO 66
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 66
ctattacgat gccagtacct tcgcttctca c          31

<210> SEQ ID NO 67

```
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 67
cgaaggtact gcaatcgtaa tagggttttt cataatc                                    37

<210> SEQ ID NO 68
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 68
ctattacgat tgcagtacct tcgcttctca c                                          31

<210> SEQ ID NO 69
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 69
cgaaggtact gtcatcgtaa tagggttttt cataatc                                    37

<210> SEQ ID NO 70
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 70
ctattacgat gacagtacct tcgcttctca c                                          31

<210> SEQ ID NO 71
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 71
cgaaggtact ctcatcgtaa tagggttttt cataatc                                    37

<210> SEQ ID NO 72
<211> LENGTH: 37
<212> TYPE: DNA
<213> ORGANISM: Artificial Sequence
<220> FEATURE:
```

```
<223> OTHER INFORMATION: synthetic
<220> FEATURE:
<221> NAME/KEY: misc_feature
<223> OTHER INFORMATION: Primer

<400> SEQUENCE: 72
ctattacgat gagagtacct tcgcttctca cttttac                              37

<210> SEQ ID NO 73
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 73
cgaaggtact gaaatcgtaa tagggtttt cataatc                              37

<210> SEQ ID NO 74
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 74
ctattacgat ttcagtacct tcgcttctca c                                   31

<210> SEQ ID NO 75
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 75
cgaaggtact accatcgtaa tagggtttt cataatc                              37

<210> SEQ ID NO 76
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 76
ctattacgat ggtagtacct tcgcttctca cttttac                             37

<210> SEQ ID NO 77
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer
```

```
<400> SEQUENCE: 77
cgaaggtact gtgatcgtaa tagggtttt cataatc                              37

<210> SEQ ID NO 78
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 78
ctattacgat cacagtacct tcgcttctca c                                   31

<210> SEQ ID NO 79
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 79
cgaaggtact gatatcgtaa tagggtttt cataatc                              37

<210> SEQ ID NO 80
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 80
ctattacgat atcagtacct tcgcttctca c                                   31

<210> SEQ ID NO 81
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 81
cgaaggtact cttatcgtaa tagggtttt cataatc                              37

<210> SEQ ID NO 82
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 82
ctattacgat aagagtacct tcgcttctca cttttac                             37
```

<210> SEQ ID NO 83
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 83
cgaaggtact caaatcgtaa tagggtttt cataatc                37

<210> SEQ ID NO 84
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 84
ctattacgat ttgagtacct tcgcttctca cttttac                37

<210> SEQ ID NO 85
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 85
cgaaggtact catatcgtaa tagggtttt cataatc                37

<210> SEQ ID NO 86
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 86
ctattacgat atgagtacct tcgcttctca cttttac                37

<210> SEQ ID NO 87
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 87
cgaaggtact tggatcgtaa tagggtttt cataatc                37

<210> SEQ ID NO 88
<211> LENGTH: 37

```
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 88
ctattacgat ccaagtacct tcgcttctca cttttac                              37

<210> SEQ ID NO 89
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 89
cgaaggtact ttgatcgtaa tagggttttt cataatc                              37

<210> SEQ ID NO 90
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 90
ctattacgat caaagtacct tcgcttctca cttttac                              37

<210> SEQ ID NO 91
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 91
cgaaggtact tctatcgtaa tagggttttt cataatc                              37

<210> SEQ ID NO 92
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 92
ctattacgat agaagtacct tcgcttctca cttttac                              37

<210> SEQ ID NO 93
<211> LENGTH: 37
<212> TYPE: DNA
<213> ORGANISM: Artificial Sequence
<220> FEATURE:
<223> OTHER INFORMATION: synthetic
```

```
<220> FEATURE:
<221> NAME/KEY: misc_feature
<223> OTHER INFORMATION: Primer

<400> SEQUENCE: 93
cgaaggtact ggtatcgtaa tagggttttt cataatc                              37

<210> SEQ ID NO 94
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 94
ctattacgat accagtacct tcgcttctca c                                    31

<210> SEQ ID NO 95
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 95
cgaaggtact gacatcgtaa tagggttttt cataatc                              37

<210> SEQ ID NO 96
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 96
ctattacgat gtcagtacct tcgcttctca c                                    31

<210> SEQ ID NO 97
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 97
cgaaggtact ccaatcgtaa tagggttttt cataatc                              37

<210> SEQ ID NO 98
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer
```

```
<400> SEQUENCE: 98
ctattacgat tggagtacct tcgcttctca cttttac                              37

<210> SEQ ID NO 99
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 99
cgaaggtact gtaatcgtaa tagggtttt cataatc                               37

<210> SEQ ID NO 100
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Primer

<400> SEQUENCE: 100
ctattacgat tacagtacct tcgcttctca c                                    31
```